(12) United States Patent
Li et al.

(10) Patent No.: US 9,382,296 B2
(45) Date of Patent: Jul. 5, 2016

(54) TRUNCATED L1 PROTEIN OF HUMAN PAPILLOMAVIRUS TYPE 58

(75) Inventors: Shaowei Li, Xiamen (CN); Minxi Wei, Xiamen (CN); Xianglin Kong, Xiamen (CN); Yingbin Wang, Xiamen (CN); Jun Zhang, Xiamen (CN); Ningshao Xia, Xiamen (CN)

(73) Assignees: XIAMEN UNIVERSITY, Fujian Province (CN); XIAMEN INNOVAX BIOTECH CO., LTD., Fujian (CN)

( * ) Notice: Subject to any disclaimer, the term of this patent is extended or adjusted under 35 U.S.C. 154(b) by 49 days.

(21) Appl. No.: 13/810,581
(22) PCT Filed: Jul. 15, 2011
(86) PCT No.: PCT/CN2011/077184
§ 371 (c)(1),
(2), (4) Date: Mar. 27, 2013
(87) PCT Pub. No.: WO2012/006962
PCT Pub. Date: Jan. 19, 2012

(65) Prior Publication Data
US 2013/0315943 A1 Nov. 28, 2013

(30) Foreign Application Priority Data
Jul. 16, 2010 (CN) .......................... 2010 1 0232875

(51) Int. Cl.
*C07K 14/025* (2006.01)
*A61K 39/12* (2006.01)
*C07K 14/005* (2006.01)
*A61K 39/00* (2006.01)
*A61K 38/00* (2006.01)

(52) U.S. Cl.
CPC .............. *C07K 14/005* (2013.01); *A61K 39/12* (2013.01); *A61K 38/00* (2013.01); *A61K 2039/5258* (2013.01); *A61K 2039/585* (2013.01); *C12N 2710/20022* (2013.01); *C12N 2710/20023* (2013.01); *C12N 2710/20034* (2013.01)

(58) Field of Classification Search
None
See application file for complete search history.

(56) References Cited

U.S. PATENT DOCUMENTS

2003/0118609 A1 6/2003 Chen
2007/0036824 A1* 2/2007 Bryan et al. ............... 424/204.1

FOREIGN PATENT DOCUMENTS

| CN | 1942583 A | 4/2007 |
| CN | 101518647 A | 9/2009 |
| CN | 101857870 A | 10/2010 |
| WO | 2005047315 A2 | 5/2005 |

OTHER PUBLICATIONS

Fey et al. Demonstration of In Vitro Synthesis of Human Papilloma Viral Proteins from Hand and Foot Warts. J Invest Dermatol. Jun. 1989;92(6):817-24.*
Machine English translation of CN 101153280 A.*
Kozak. Point Mutations Define a Sequence Flanking the AUG Initiator Codon That Modulates Translation by Eukaryotic Ribosomes. Cell, vol. 44, 283-292, Jan. 31, 1986.*
Zemskovaa et al. Transient expression of deletion mutants of the herpes simplex virus thymidine kinase-encoding gene in mouse fibroblast cells. Gene. Volume 106, Issue 2, Oct. 15.*
Chen et al. (J. Mol. Biol. (2001) 307, 173-182).*
International Search Report for PCT/CN2011/077184 mailed Oct. 27, 2011.
Li et al., "Carboxyl Terminus Truncated HPV58 Virus L1 Protein Expressed with Baculovirus System and its Bioactivity," Chinese Journal of Biotechnology, Jul. 2004, vol. 20, No. 4, pp. 536-539 (Abstract).
Needleman & Wunsch, "A general method applicable to the search for similarities in the amino acid sequence of two proteins," J. Mol. Biol. 48, 445-53, 1970.
Boyle & Ferlay, "Cancer incidence and mortality in Europe," Ann. Oncol. 16, 481-88, 2005.
Kelsall & Kulski "Expression of the major capsid protein of human papillomavirus type 16 in *Eschericia coli*," J. Virol. Meth. 53, 75-90, 1995.
Banks et al., "Expression of human papillomavirus type 6 and type 16 capsid proteins in bacteria and their antigenic characterization," J. Gen. Virol. 68, 3081-89, 1987.
Li et al., "Expression of the Human Papillomavirus Type 11 L1 Capsid Protein in *Escherichia coli* Characterization of Protein Domains Involved in DNA Binding and Capsid Assembly," J. Virol. 71, 2988095, 1997.
Bao et al., "Human papillomavirus type-distribution in the cervix of Chinese women: a meta-analysis,"Int. J. STD & AIDS 19, 106-11, 2007.
Clifford et al., "Human papillomavirus types in invasive cervical cancer worldwide: a meta analysis," Br. J. Cancer 88, 63-73, 2003.
Burks et al., "In vitro scanning saturation mutagenesis of an antibody binding pocket," Proc. Nat'l. Acad. Sci. USA 94, 412-17, 1997.
Myers & Miller, "Optimal alignments in linear space," Comput. Appl. Biosci. 4, 11-17, 1988.
Kirnbauer et al., "Papillomavirus L1 major capsid protein self-assembles into virus-like particles that are highly immunogenic," Proc. Nat'l. Acad. Sci. USA 89, 12188-84, 1992.
Brummell et al., "Probing the combining site of an anti-carbohydrate antibody by saturation-mutagenesis role of the heavy-chain CDR3 residues," Biochem. 32, 1180-87, 1993.
Kobayashi et al., "Tryptophan H33 plays an important role in pyrimidine (6-4) pyrimidone photoproduct binding by a high-affinity antibody," Prot. Eng. 12, 879-84, 1999.
Li et al., "Carboxyl Terminus Truncated HPV58 Virus L1 Protein Expression with Baculovirus System and Its Bioactivity," Ch. J. Biotechnol. 20, 536-39, 2004; English abstract p. 539.
Database UniParc [Online], Database Accession No. UPI0001A4DFE6, May 25, 2009, XP002715983 (http://www.uniprot.org/uniparc/UPI0001A4DFE6, Jun. 11, 2013).

(Continued)

*Primary Examiner* — Nick Zou
(74) *Attorney, Agent, or Firm* — Banner & Witcoff, Ltd.

(57) ABSTRACT

Provided are an N-terminal truncated L1 protein of the Human Papillomavirus Type 58, a coding sequence and preparation method thereof, and a virus-like particle comprising the protein. Uses of the protein and the virus-like particle in the preparation of a pharmaceutical composition or a vaccine are further provided. The pharmaceutical composition or vaccine is used for prevention of HPV infection and a disease caused by HPV infection.

9 Claims, 9 Drawing Sheets

(56) References Cited

OTHER PUBLICATIONS

Extended European Search Report for EP Application No. 11806304. 9, dated Dec. 11, 2013.

Fu et al., "New human papilioma virus (HPV)58L1 gene, useful for biological applications," Database WPI, XP002715985.

Kirii et al., "Human Papillomavirus Type 58 Complete Genome," Virology, 1991, vol. 185, No. 1, pp. 424-427, Database Nucleotide [Online], Dec. 7, 2007, Database Accession No. D90400.1, XP002715984.

Li et al., "[Carboxyl terminus truncated HPV58 virus L1 protein expressed with baculovirus system and its bioactivity]," Jul. 2004, Database accession No. NLM15968984, XP-002715989.

Wang et al., "Translational comparison of HPV58 long and short L1 mRNAs in yeast (*Saccharomyces cerevisiae*) cellfree system," Journal of Bioscience and Bioengineering, 2010, vol. 110, No. 1, pp. 58-65.

* cited by examiner

SEQUENCE LISTING

<160> NUMBER OF SEQ ID NOS: 17

<210> SEQ ID NO 1
<211> LENGTH: 491
<212> TYPE: PRT
<213> ORGANISM: Artificial Sequence
<220> FEATURE:
<223> OTHER INFORMATION: truncated HPV58 L1 protein

<400> SEQUENCE: 1

```
Pro Met Thr Val Tyr Leu Pro Pro Val Pro Val Ser Lys Val Val Ser
1               5                   10                  15

Thr Asp Glu Tyr Val Ser Arg Thr Ser Ile Tyr Tyr Ala Gly Ser
            20                  25                  30

Ser Arg Leu Leu Ala Val Gly Asn Pro Tyr Phe Ser Ile Lys Ser Pro
        35                  40                  45

Asn Asn Asn Lys Lys Val Leu Val Pro Lys Val Ser Gly Leu Gln Tyr
    50                  55                  60

Arg Val Phe Arg Val Arg Leu Pro Asp Pro Asn Lys Phe Gly Phe Pro
65                  70                  75                  80

Asp Thr Ser Phe Tyr Asn Pro Asp Thr Gln Arg Leu Val Trp Ala Cys
                85                  90                  95

Val Gly Leu Glu Ile Gly Arg Gly Gln Pro Leu Gly Val Gly Val Ser
            100                 105                 110

Gly His Pro Tyr Leu Asn Lys Phe Asp Asp Thr Glu Thr Ser Asn Arg
        115                 120                 125

Tyr Pro Ala Gln Pro Gly Ser Asp Asn Arg Glu Cys Leu Ser Met Asp
    130                 135                 140

Tyr Lys Gln Thr Gln Leu Cys Leu Ile Gly Cys Lys Pro Pro Thr Gly
145                 150                 155                 160

Glu His Trp Gly Lys Gly Val Ala Cys Asn Asn Asn Ala Ala Ala Thr
                165                 170                 175

Asp Cys Pro Pro Leu Glu Leu Phe Asn Ser Ile Ile Glu Asp Gly Asp
            180                 185                 190

Met Val Asp Thr Gly Phe Gly Cys Met Asp Phe Gly Thr Leu Gln Ala
        195                 200                 205

Asn Lys Ser Asp Val Pro Ile Asp Ile Cys Asn Ser Thr Cys Lys Tyr
    210                 215                 220

Pro Asp Tyr Leu Lys Met Ala Ser Glu Pro Tyr Gly Asp Ser Leu Phe
225                 230                 235                 240

Phe Phe Leu Arg Arg Glu Gln Met Phe Val Arg His Phe Phe Asn Arg
                245                 250                 255

Ala Gly Lys Leu Gly Glu Ala Val Pro Asp Asp Leu Tyr Ile Lys Gly
            260                 265                 270

Ser Gly Asn Thr Ala Val Ile Gln Ser Ser Ala Phe Phe Pro Thr Pro
        275                 280                 285

Ser Gly Ser Ile Val Thr Ser Glu Ser Gln Leu Phe Asn Lys Pro Tyr
    290                 295                 300

Trp Leu Gln Arg Ala Gln Gly His Asn Asn Gly Ile Cys Trp Gly Asn
305                 310                 315                 320

Gln Leu Phe Val Thr Val Val Asp Thr Thr Arg Ser Thr Asn Met Thr
                325                 330                 335

Leu Cys Thr Glu Val Thr Lys Glu Gly Thr Tyr Lys Asn Asp Asn Phe
            340                 345                 350

Lys Glu Tyr Val Arg His Val Glu Glu Tyr Asp Leu Gln Phe Val Phe
```

```
            355                 360                 365
Gln Leu Cys Lys Ile Thr Leu Thr Ala Glu Ile Met Thr Tyr Ile His
    370                 375                 380

Thr Met Asp Ser Asn Ile Leu Glu Asp Trp Gln Phe Gly Leu Thr Pro
385                 390                 395                 400

Pro Pro Ser Ala Ser Leu Gln Asp Thr Tyr Arg Phe Val Thr Ser Gln
                405                 410                 415

Ala Ile Thr Cys Gln Lys Thr Ala Pro Pro Lys Glu Lys Glu Asp Pro
                420                 425                 430

Leu Asn Lys Tyr Thr Phe Trp Glu Val Asn Leu Lys Glu Lys Phe Ser
                435                 440                 445

Ala Asp Leu Asp Gln Phe Pro Leu Gly Arg Lys Phe Leu Leu Gln Ser
            450                 455                 460

Gly Leu Lys Ala Lys Pro Arg Leu Lys Arg Ser Ala Pro Thr Thr Arg
465                 470                 475                 480

Ala Pro Ser Thr Lys Arg Lys Lys Val Lys Lys
                485                 490

<210> SEQ ID NO 2
<211> LENGTH: 521
<212> TYPE: PRT
<213> ORGANISM: Artificial Sequence
<220> FEATURE:
<223> OTHER INFORMATION: truncated HPV58 L1 protein

<400> SEQUENCE: 2

Pro Met Cys Cys Thr Leu Ala Ile Leu Phe Cys Val Ala Asp Val Asn
1               5                   10                  15

Val Phe His Ile Phe Leu Gln Met Ser Val Trp Arg Pro Ser Glu Ala
                20                  25                  30

Thr Val Tyr Leu Pro Pro Val Pro Val Ser Lys Val Val Ser Thr Asp
            35                  40                  45

Glu Tyr Val Ser Arg Thr Ser Ile Tyr Tyr Tyr Ala Gly Ser Ser Arg
    50                  55                  60

Leu Leu Ala Val Gly Asn Pro Tyr Phe Ser Ile Lys Ser Pro Asn Asn
65                  70                  75                  80

Asn Lys Lys Val Leu Val Pro Lys Val Ser Gly Leu Gln Tyr Arg Val
                85                  90                  95

Phe Arg Val Arg Leu Pro Asp Pro Asn Lys Phe Gly Phe Pro Asp Thr
                100                 105                 110

Ser Phe Tyr Asn Pro Asp Thr Gln Arg Leu Val Trp Ala Cys Val Gly
            115                 120                 125

Leu Glu Ile Gly Arg Gly Gln Pro Leu Gly Val Gly Val Ser Gly His
    130                 135                 140

Pro Tyr Leu Asn Lys Phe Asp Asp Thr Glu Thr Ser Asn Arg Tyr Pro
145                 150                 155                 160

Ala Gln Pro Gly Ser Asp Asn Arg Glu Cys Leu Ser Met Asp Tyr Lys
                165                 170                 175

Gln Thr Gln Leu Cys Leu Ile Gly Cys Lys Pro Pro Thr Gly Glu His
            180                 185                 190

Trp Gly Lys Gly Val Ala Cys Asn Asn Asn Ala Ala Thr Asp Cys
    195                 200                 205

Pro Pro Leu Glu Leu Phe Asn Ser Ile Ile Glu Asp Gly Asp Met Val
    210                 215                 220

Asp Thr Gly Phe Gly Cys Met Asp Phe Gly Thr Leu Gln Ala Asn Lys
```

```
                225                 230                 235                 240
        Ser Asp Val Pro Ile Asp Ile Cys Asn Ser Thr Cys Lys Tyr Pro Asp
                        245                 250                 255

Tyr Leu Lys Met Ala Ser Glu Pro Tyr Gly Asp Ser Leu Phe Phe Phe
                        260                 265                 270

Leu Arg Arg Glu Gln Met Phe Val Arg His Phe Phe Asn Arg Ala Gly
                        275                 280                 285

Lys Leu Gly Glu Ala Val Pro Asp Asp Leu Tyr Ile Lys Gly Ser Gly
                        290                 295                 300

Asn Thr Ala Val Ile Gln Ser Ser Ala Phe Phe Pro Thr Pro Ser Gly
        305                 310                 315                 320

Ser Ile Val Thr Ser Glu Ser Gln Leu Phe Asn Lys Pro Tyr Trp Leu
                        325                 330                 335

Gln Arg Ala Gln Gly His Asn Asn Gly Ile Cys Trp Gly Asn Gln Leu
                        340                 345                 350

Phe Val Thr Val Val Asp Thr Thr Arg Ser Thr Asn Met Thr Leu Cys
                        355                 360                 365

Thr Glu Val Thr Lys Glu Gly Thr Tyr Lys Asn Asp Asn Phe Lys Glu
                        370                 375                 380

Tyr Val Arg His Val Glu Glu Tyr Asp Leu Gln Phe Val Phe Gln Leu
        385                 390                 395                 400

Cys Lys Ile Thr Leu Thr Ala Glu Ile Met Thr Tyr Ile His Thr Met
                        405                 410                 415

Asp Ser Asn Ile Leu Glu Asp Trp Gln Phe Gly Leu Thr Pro Pro Pro
                        420                 425                 430

Ser Ala Ser Leu Gln Asp Thr Tyr Arg Phe Val Thr Ser Gln Ala Ile
                        435                 440                 445

Thr Cys Gln Lys Thr Ala Pro Pro Lys Glu Lys Glu Asp Pro Leu Asn
                        450                 455                 460

Lys Tyr Thr Phe Trp Glu Val Asn Leu Lys Glu Lys Phe Ser Ala Asp
        465                 470                 475                 480

Leu Asp Gln Phe Pro Leu Gly Arg Lys Phe Leu Leu Gln Ser Gly Leu
                        485                 490                 495

Lys Ala Lys Pro Arg Leu Lys Arg Ser Ala Pro Thr Thr Arg Ala Pro
                        500                 505                 510

Ser Thr Lys Arg Lys Val Lys Lys
                        515                 520

<210> SEQ ID NO 3
<211> LENGTH: 511
<212> TYPE: PRT
<213> ORGANISM: Artificial Sequence
<220> FEATURE:
<223> OTHER INFORMATION: truncated HPV58 L1 protein

<400> SEQUENCE: 3

Pro Met Ala Asp Val Asn Val Phe His Ile Phe Leu Gln Met Ser Val
        1               5                   10                  15

Trp Arg Pro Ser Glu Ala Thr Val Tyr Leu Pro Pro Val Pro Val Ser
                        20                  25                  30

Lys Val Val Ser Thr Asp Glu Tyr Val Ser Arg Thr Ser Ile Tyr Tyr
                        35                  40                  45

Tyr Ala Gly Ser Ser Arg Leu Leu Ala Val Gly Asn Pro Tyr Phe Ser
                        50                  55                  60

Ile Lys Ser Pro Asn Asn Asn Lys Lys Val Leu Val Pro Lys Val Ser
```

```
                65                  70                  75                  80
        Gly Leu Gln Tyr Arg Val Phe Arg Val Arg Leu Pro Asp Pro Asn Lys
                            85                  90                  95
        Phe Gly Phe Pro Asp Thr Ser Phe Tyr Asn Pro Asp Thr Gln Arg Leu
                           100                 105                 110
        Val Trp Ala Cys Val Gly Leu Glu Ile Gly Arg Gly Gln Pro Leu Gly
                           115                 120                 125
        Val Gly Val Ser Gly His Pro Tyr Leu Asn Lys Phe Asp Asp Thr Glu
                   130                 135                 140
        Thr Ser Asn Arg Tyr Pro Ala Gln Pro Gly Ser Asp Asn Arg Glu Cys
        145                 150                 155                 160
        Leu Ser Met Asp Tyr Lys Gln Thr Gln Leu Cys Leu Ile Gly Cys Lys
                           165                 170                 175
        Pro Pro Thr Gly Glu His Trp Gly Lys Gly Val Ala Cys Asn Asn Asn
                   180                 185                 190
        Ala Ala Ala Thr Asp Cys Pro Pro Leu Glu Leu Phe Asn Ser Ile Ile
                   195                 200                 205
        Glu Asp Gly Asp Met Val Asp Thr Gly Phe Gly Cys Met Asp Phe Gly
                   210                 215                 220
        Thr Leu Gln Ala Asn Lys Ser Asp Val Pro Ile Asp Ile Cys Asn Ser
        225                 230                 235                 240
        Thr Cys Lys Tyr Pro Asp Tyr Leu Lys Met Ala Ser Glu Pro Tyr Gly
                           245                 250                 255
        Asp Ser Leu Phe Phe Phe Leu Arg Arg Glu Gln Met Phe Val Arg His
                           260                 265                 270
        Phe Phe Asn Arg Ala Gly Lys Leu Gly Glu Ala Val Pro Asp Asp Leu
                   275                 280                 285
        Tyr Ile Lys Gly Ser Gly Asn Thr Ala Val Ile Gln Ser Ser Ala Phe
                   290                 295                 300
        Phe Pro Thr Pro Ser Gly Ser Ile Val Thr Ser Glu Ser Gln Leu Phe
        305                 310                 315                 320
        Asn Lys Pro Tyr Trp Leu Gln Arg Ala Gln Gly His Asn Asn Gly Ile
                           325                 330                 335
        Cys Trp Gly Asn Gln Leu Phe Val Thr Val Val Asp Thr Thr Arg Ser
                           340                 345                 350
        Thr Asn Met Thr Leu Cys Thr Glu Val Thr Lys Glu Gly Thr Tyr Lys
                   355                 360                 365
        Asn Asp Asn Phe Lys Glu Tyr Val Arg His Val Glu Glu Tyr Asp Leu
                   370                 375                 380
        Gln Phe Val Phe Gln Leu Cys Lys Ile Thr Leu Thr Ala Glu Ile Met
        385                 390                 395                 400
        Thr Tyr Ile His Thr Met Asp Ser Asn Ile Leu Glu Asp Trp Gln Phe
                           405                 410                 415
        Gly Leu Thr Pro Pro Ser Ala Ser Leu Gln Asp Thr Tyr Arg Phe
                           420                 425                 430
        Val Thr Ser Gln Ala Ile Thr Cys Gln Lys Thr Ala Pro Pro Lys Glu
                   435                 440                 445
        Lys Glu Asp Pro Leu Asn Lys Tyr Thr Phe Trp Glu Val Asn Leu Lys
                   450                 455                 460
        Glu Lys Phe Ser Ala Asp Leu Asp Gln Phe Pro Leu Gly Arg Lys Phe
        465                 470                 475                 480
        Leu Leu Gln Ser Gly Leu Lys Ala Lys Pro Arg Leu Lys Arg Ser Ala
                           485                 490                 495
```

Pro Thr Thr Arg Ala Pro Ser Thr Lys Arg Lys Val Lys Lys
            500                 505                 510

<210> SEQ ID NO 4
<211> LENGTH: 499
<212> TYPE: PRT
<213> ORGANISM: Artificial Sequence
<220> FEATURE:
<223> OTHER INFORMATION: truncated HPV58 L1 protein

<400> SEQUENCE: 4

Pro Met Ser Val Trp Arg Pro Ser Glu Ala Thr Val Tyr Leu Pro Pro
1               5                   10                  15

Val Pro Val Ser Lys Val Val Ser Thr Asp Glu Tyr Val Ser Arg Thr
            20                  25                  30

Ser Ile Tyr Tyr Tyr Ala Gly Ser Ser Arg Leu Leu Ala Val Gly Asn
        35                  40                  45

Pro Tyr Phe Ser Ile Lys Ser Pro Asn Asn Asn Lys Lys Val Leu Val
    50                  55                  60

Pro Lys Val Ser Gly Leu Gln Tyr Arg Val Phe Arg Val Arg Leu Pro
65                  70                  75                  80

Asp Pro Asn Lys Phe Gly Phe Pro Asp Thr Ser Phe Tyr Asn Pro Asp
                85                  90                  95

Thr Gln Arg Leu Val Trp Ala Cys Val Gly Leu Glu Ile Gly Arg Gly
            100                 105                 110

Gln Pro Leu Gly Val Gly Val Ser Gly His Pro Tyr Leu Asn Lys Phe
        115                 120                 125

Asp Asp Thr Glu Thr Ser Asn Arg Tyr Pro Ala Gln Pro Gly Ser Asp
    130                 135                 140

Asn Arg Glu Cys Leu Ser Met Asp Tyr Lys Gln Thr Gln Leu Cys Leu
145                 150                 155                 160

Ile Gly Cys Lys Pro Pro Thr Gly Glu His Trp Gly Lys Gly Val Ala
                165                 170                 175

Cys Asn Asn Asn Ala Ala Ala Thr Asp Cys Pro Pro Leu Glu Leu Phe
            180                 185                 190

Asn Ser Ile Ile Glu Asp Gly Asp Met Val Asp Thr Gly Phe Gly Cys
        195                 200                 205

Met Asp Phe Gly Thr Leu Gln Ala Asn Lys Ser Asp Val Pro Ile Asp
    210                 215                 220

Ile Cys Asn Ser Thr Cys Lys Tyr Pro Asp Tyr Leu Lys Met Ala Ser
225                 230                 235                 240

Glu Pro Tyr Gly Asp Ser Leu Phe Phe Phe Leu Arg Arg Glu Gln Met
                245                 250                 255

Phe Val Arg His Phe Phe Asn Arg Ala Gly Lys Leu Gly Glu Ala Val
            260                 265                 270

Pro Asp Asp Leu Tyr Ile Lys Gly Ser Gly Asn Thr Ala Val Ile Gln
        275                 280                 285

Ser Ser Ala Phe Phe Pro Thr Pro Ser Gly Ser Ile Val Thr Ser Glu
    290                 295                 300

Ser Gln Leu Phe Asn Lys Pro Tyr Trp Leu Gln Arg Ala Gln Gly His
305                 310                 315                 320

Asn Asn Gly Ile Cys Trp Gly Asn Gln Leu Phe Val Thr Val Val Asp
                325                 330                 335

Thr Thr Arg Ser Thr Asn Met Thr Leu Cys Thr Glu Val Thr Lys Glu
            340                 345                 350

```
Gly Thr Tyr Lys Asn Asp Asn Phe Lys Glu Tyr Val Arg His Val Glu
            355                 360                 365

Glu Tyr Asp Leu Gln Phe Val Phe Gln Leu Cys Lys Ile Thr Leu Thr
        370                 375                 380

Ala Glu Ile Met Thr Tyr Ile His Thr Met Asp Ser Asn Ile Leu Glu
385                 390                 395                 400

Asp Trp Gln Phe Gly Leu Thr Pro Pro Ser Ala Ser Leu Gln Asp
            405                 410                 415

Thr Tyr Arg Phe Val Thr Ser Gln Ala Ile Thr Cys Gln Lys Thr Ala
            420                 425                 430

Pro Pro Lys Glu Lys Glu Asp Pro Leu Asn Lys Tyr Thr Phe Trp Glu
            435                 440                 445

Val Asn Leu Lys Glu Lys Phe Ser Ala Asp Leu Asp Gln Phe Pro Leu
        450                 455                 460

Gly Arg Lys Phe Leu Leu Gln Ser Gly Leu Lys Ala Lys Pro Arg Leu
465                 470                 475                 480

Lys Arg Ser Ala Pro Thr Thr Arg Ala Pro Ser Thr Lys Arg Lys Lys
                485                 490                 495

Val Lys Lys

<210> SEQ ID NO 5
<211> LENGTH: 486
<212> TYPE: PRT
<213> ORGANISM: Artificial Sequence
<220> FEATURE:
<223> OTHER INFORMATION: truncated HPV58 L1 protein

<400> SEQUENCE: 5

Pro Met Pro Val Pro Val Ser Lys Val Val Ser Thr Asp Glu Tyr Val
1               5                   10                  15

Ser Arg Thr Ser Ile Tyr Tyr Tyr Ala Gly Ser Ser Arg Leu Leu Ala
            20                  25                  30

Val Gly Asn Pro Tyr Phe Ser Ile Lys Ser Pro Asn Asn Asn Lys Lys
        35                  40                  45

Val Leu Val Pro Lys Val Ser Gly Leu Gln Tyr Arg Val Phe Arg Val
    50                  55                  60

Arg Leu Pro Asp Pro Asn Lys Phe Gly Phe Pro Asp Thr Ser Phe Tyr
65                  70                  75                  80

Asn Pro Asp Thr Gln Arg Leu Val Trp Ala Cys Val Gly Leu Glu Ile
                85                  90                  95

Gly Arg Gly Gln Pro Leu Gly Val Gly Val Ser Gly His Pro Tyr Leu
            100                 105                 110

Asn Lys Phe Asp Asp Thr Glu Thr Ser Asn Arg Tyr Pro Ala Gln Pro
        115                 120                 125

Gly Ser Asp Asn Arg Glu Cys Leu Ser Met Asp Tyr Lys Gln Thr Gln
    130                 135                 140

Leu Cys Leu Ile Gly Cys Lys Pro Pro Thr Gly Glu His Trp Gly Lys
145                 150                 155                 160

Gly Val Ala Cys Asn Asn Asn Ala Ala Ala Thr Asp Cys Pro Pro Leu
                165                 170                 175

Glu Leu Phe Asn Ser Ile Ile Glu Asp Gly Asp Met Val Asp Thr Gly
            180                 185                 190

Phe Gly Cys Met Asp Phe Gly Thr Leu Gln Ala Asn Lys Ser Asp Val
        195                 200                 205
```

```
Pro Ile Asp Ile Cys Asn Ser Thr Cys Lys Tyr Pro Asp Tyr Leu Lys
    210                 215                 220

Met Ala Ser Glu Pro Tyr Gly Asp Ser Leu Phe Phe Phe Leu Arg Arg
225                 230                 235                 240

Glu Gln Met Phe Val Arg His Phe Phe Asn Arg Ala Gly Lys Leu Gly
                245                 250                 255

Glu Ala Val Pro Asp Asp Leu Tyr Ile Lys Gly Ser Gly Asn Thr Ala
                260                 265                 270

Val Ile Gln Ser Ser Ala Phe Phe Pro Thr Pro Ser Gly Ser Ile Val
            275                 280                 285

Thr Ser Glu Ser Gln Leu Phe Asn Lys Pro Tyr Trp Leu Gln Arg Ala
290                 295                 300

Gln Gly His Asn Asn Gly Ile Cys Trp Gly Asn Gln Leu Phe Val Thr
305                 310                 315                 320

Val Val Asp Thr Thr Arg Ser Thr Asn Met Thr Leu Cys Thr Glu Val
                325                 330                 335

Thr Lys Glu Gly Thr Tyr Lys Asn Asp Asn Phe Lys Glu Tyr Val Arg
                340                 345                 350

His Val Glu Glu Tyr Asp Leu Gln Phe Val Phe Gln Leu Cys Lys Ile
            355                 360                 365

Thr Leu Thr Ala Glu Ile Met Thr Tyr Ile His Thr Met Asp Ser Asn
370                 375                 380

Ile Leu Glu Asp Trp Gln Phe Gly Leu Thr Pro Pro Pro Ser Ala Ser
385                 390                 395                 400

Leu Gln Asp Thr Tyr Arg Phe Val Thr Ser Gln Ala Ile Thr Cys Gln
                405                 410                 415

Lys Thr Ala Pro Pro Lys Glu Lys Glu Asp Pro Leu Asn Lys Tyr Thr
                420                 425                 430

Phe Trp Glu Val Asn Leu Lys Glu Lys Phe Ser Ala Asp Leu Asp Gln
            435                 440                 445

Phe Pro Leu Gly Arg Lys Phe Leu Leu Gln Ser Gly Leu Lys Ala Lys
            450                 455                 460

Pro Arg Leu Lys Arg Ser Ala Pro Thr Thr Arg Ala Pro Ser Thr Lys
465                 470                 475                 480

Arg Lys Lys Val Lys Lys
                485

<210> SEQ ID NO 6
<211> LENGTH: 466
<212> TYPE: PRT
<213> ORGANISM: Artificial Sequence
<220> FEATURE:
<223> OTHER INFORMATION: truncated HPV58 L1 protein

<400> SEQUENCE: 6

Pro Met Tyr Tyr Ala Gly Ser Ser Arg Leu Leu Ala Val Gly Asn Pro
1               5                   10                  15

Tyr Phe Ser Ile Lys Ser Pro Asn Asn Asn Lys Lys Val Leu Val Pro
            20                  25                  30

Lys Val Ser Gly Leu Gln Tyr Arg Val Phe Arg Val Arg Leu Pro Asp
        35                  40                  45

Pro Asn Lys Phe Gly Phe Pro Asp Thr Ser Phe Tyr Asn Pro Asp Thr
    50                  55                  60

Gln Arg Leu Val Trp Ala Cys Val Gly Leu Glu Ile Gly Arg Gly Gln
65                  70                  75                  80
```

```
Pro Leu Gly Val Gly Val Ser Gly His Pro Tyr Leu Asn Lys Phe Asp
                85                  90                  95
Asp Thr Glu Thr Ser Asn Arg Tyr Pro Ala Gln Pro Gly Ser Asp Asn
            100                 105                 110
Arg Glu Cys Leu Ser Met Asp Tyr Lys Gln Thr Gln Leu Cys Leu Ile
        115                 120                 125
Gly Cys Lys Pro Pro Thr Gly Glu His Trp Gly Lys Gly Val Ala Cys
    130                 135                 140
Asn Asn Asn Ala Ala Ala Thr Asp Cys Pro Pro Leu Glu Leu Phe Asn
145                 150                 155                 160
Ser Ile Ile Glu Asp Gly Asp Met Val Asp Thr Gly Phe Gly Cys Met
                165                 170                 175
Asp Phe Gly Thr Leu Gln Ala Asn Lys Ser Asp Val Pro Ile Asp Ile
            180                 185                 190
Cys Asn Ser Thr Cys Lys Tyr Pro Asp Tyr Leu Lys Met Ala Ser Glu
        195                 200                 205
Pro Tyr Gly Asp Ser Leu Phe Phe Leu Arg Arg Glu Gln Met Phe
    210                 215                 220
Val Arg His Phe Phe Asn Arg Ala Gly Lys Leu Gly Glu Ala Val Pro
225                 230                 235                 240
Asp Asp Leu Tyr Ile Lys Gly Ser Gly Asn Thr Ala Val Ile Gln Ser
                245                 250                 255
Ser Ala Phe Phe Pro Thr Pro Ser Gly Ser Ile Val Thr Ser Glu Ser
            260                 265                 270
Gln Leu Phe Asn Lys Pro Tyr Trp Leu Gln Arg Ala Gln Gly His Asn
        275                 280                 285
Asn Gly Ile Cys Trp Gly Asn Gln Leu Phe Val Thr Val Val Asp Thr
    290                 295                 300
Thr Arg Ser Thr Asn Met Thr Leu Cys Thr Glu Val Thr Lys Glu Gly
305                 310                 315                 320
Thr Tyr Lys Asn Asp Asn Phe Lys Glu Tyr Val Arg His Val Glu Glu
                325                 330                 335
Tyr Asp Leu Gln Phe Val Phe Gln Leu Cys Lys Ile Thr Leu Thr Ala
            340                 345                 350
Glu Ile Met Thr Tyr Ile His Thr Met Asp Ser Asn Ile Leu Glu Asp
        355                 360                 365
Trp Gln Phe Gly Leu Thr Pro Pro Ser Ala Ser Leu Gln Asp Thr
    370                 375                 380
Tyr Arg Phe Val Thr Ser Gln Ala Ile Thr Cys Gln Lys Thr Ala Pro
385                 390                 395                 400
Pro Lys Glu Lys Glu Asp Pro Leu Asn Lys Tyr Thr Phe Trp Glu Val
                405                 410                 415
Asn Leu Lys Glu Lys Phe Ser Ala Asp Leu Asp Gln Phe Pro Leu Gly
            420                 425                 430
Arg Lys Phe Leu Leu Gln Ser Gly Leu Lys Ala Lys Pro Arg Leu Lys
        435                 440                 445
Arg Ser Ala Pro Thr Thr Arg Ala Pro Ser Thr Lys Arg Lys Lys Val
    450                 455                 460
Lys Lys
465

<210> SEQ ID NO 7
<211> LENGTH: 456
<212> TYPE: PRT
```

<213> ORGANISM: Artificial Sequence
<220> FEATURE:
<223> OTHER INFORMATION: truncated HPV58 L1 protein

<400> SEQUENCE: 7

```
Pro Met Val Gly Asn Pro Tyr Phe Ser Ile Lys Ser Pro Asn Asn Asn
1               5                   10                  15

Lys Lys Val Leu Val Pro Lys Val Ser Gly Leu Gln Tyr Arg Val Phe
            20                  25                  30

Arg Val Arg Leu Pro Asp Pro Asn Lys Phe Gly Phe Pro Asp Thr Ser
        35                  40                  45

Phe Tyr Asn Pro Asp Thr Gln Arg Leu Val Trp Ala Cys Val Gly Leu
    50                  55                  60

Glu Ile Gly Arg Gly Gln Pro Leu Gly Val Gly Val Ser Gly His Pro
65                  70                  75                  80

Tyr Leu Asn Lys Phe Asp Asp Thr Glu Thr Ser Asn Arg Tyr Pro Ala
                85                  90                  95

Gln Pro Gly Ser Asp Asn Arg Glu Cys Leu Ser Met Asp Tyr Lys Gln
            100                 105                 110

Thr Gln Leu Cys Leu Ile Gly Cys Lys Pro Pro Thr Gly Glu His Trp
        115                 120                 125

Gly Lys Gly Val Ala Cys Asn Asn Ala Ala Ala Thr Asp Cys Pro
    130                 135                 140

Pro Leu Glu Leu Phe Asn Ser Ile Ile Glu Asp Gly Asp Met Val Asp
145                 150                 155                 160

Thr Gly Phe Gly Cys Met Asp Phe Gly Thr Leu Gln Ala Asn Lys Ser
                165                 170                 175

Asp Val Pro Ile Asp Ile Cys Asn Ser Thr Cys Lys Tyr Pro Asp Tyr
            180                 185                 190

Leu Lys Met Ala Ser Glu Pro Tyr Gly Asp Ser Leu Phe Phe Phe Leu
        195                 200                 205

Arg Arg Glu Gln Met Phe Val Arg His Phe Phe Asn Arg Ala Gly Lys
    210                 215                 220

Leu Gly Glu Ala Val Pro Asp Asp Leu Tyr Ile Lys Gly Ser Gly Asn
225                 230                 235                 240

Thr Ala Val Ile Gln Ser Ser Ala Phe Phe Pro Thr Pro Ser Gly Ser
                245                 250                 255

Ile Val Thr Ser Glu Ser Gln Leu Phe Asn Lys Pro Tyr Trp Leu Gln
            260                 265                 270

Arg Ala Gln Gly His Asn Asn Gly Ile Cys Trp Gly Asn Gln Leu Phe
        275                 280                 285

Val Thr Val Val Asp Thr Thr Arg Ser Thr Asn Met Thr Leu Cys Thr
    290                 295                 300

Glu Val Thr Lys Glu Gly Thr Tyr Lys Asn Asp Asn Phe Lys Glu Tyr
305                 310                 315                 320

Val Arg His Val Glu Glu Tyr Asp Leu Gln Phe Val Phe Gln Leu Cys
                325                 330                 335

Lys Ile Thr Leu Thr Ala Glu Ile Met Thr Tyr Ile His Thr Met Asp
            340                 345                 350

Ser Asn Ile Leu Glu Asp Trp Gln Phe Gly Leu Thr Pro Pro Pro Ser
        355                 360                 365

Ala Ser Leu Gln Asp Thr Tyr Arg Phe Val Thr Ser Gln Ala Ile Thr
    370                 375                 380

Cys Gln Lys Thr Ala Pro Pro Lys Glu Lys Glu Asp Pro Leu Asn Lys
```

```
                385                 390                 395                 400
        Tyr Thr Phe Trp Glu Val Asn Leu Lys Glu Lys Phe Ser Ala Asp Leu
                        405                 410                 415

Asp Gln Phe Pro Leu Gly Arg Lys Phe Leu Leu Gln Ser Gly Leu Lys
                        420                 425                 430

Ala Lys Pro Arg Leu Lys Arg Ser Ala Pro Thr Thr Arg Ala Pro Ser
                        435                 440                 445

Thr Lys Arg Lys Lys Val Lys Lys
                        450                 455

<210> SEQ ID NO 8
<211> LENGTH: 1575
<212> TYPE: DNA
<213> ORGANISM: Artificial Sequence
<220> FEATURE:
<223> OTHER INFORMATION: coding sequence for truncated HPV58 L1 protein

<400> SEQUENCE: 8
atggtgctga tcctgtgctg caccctggcc atcctgttct gcgtggccga cgtgaacgtg      60
ttccacatct tcctgcagat gagcgtgtgg aggcccagcg aggccaccgt gtacctgccc     120
cccgtgcccg tgagcaaggt ggtgagcacc gacgagtacg tgagcaggac cagcatctac     180
tactacgccg gcagcagcag gctgctggcc gtgggcaacc cctacttcag catcaagagc     240
cccaacaaca caaggaaggt gctggtgccc aaggtgagcg gcctgcagta cagggtgttc     300
agggtgaggc tgcccgaccc caacaagttc ggcttccccg acaccagctt ctacaacccc     360
gacacccaga ggctggtgtg ggcctgcgtg ggcctggaga tcggcagggg ccagcccctg     420
ggcgtgggcg tgagcggcca ccccctacctg aacaagttcg acgacaccga ccagcaac     480 aggtaccccg cccagcccgg cagcgacaac agggagtgcc tgagcatgga ctacaagcag     540
acccagctgt gcctgatcgg ctgcaagccc cccaccggcg agcactgggg caagggcgtg     600
gcctgcaaca caacgccgc cgccaccgac tgccccccc tggagctgtt caacagcatc     660
atcgaggacg gcgacatggt ggacaccggc ttcggctgca tggacttcgg caccctgcag     720
gccaacaaga gcgacgtgcc catcgacatc tgcaacagca cctgcaagta ccccgactac     780
ctgaagatgg ccagcgagcc ctacggcgac agcctgttct tcttcctgag gagggagcag     840
atgttcgtga ggcacttctt caacagggcc ggcaagctgg gcgaggccgt gcccgacgac     900
ctgtacatca agggcagcgg caacaccgcc gtgatccaga gcagcgcctt cttccccacc     960
cccagcggca gcatcgtgac cagcgagagc cagctgttca acaagcccta ctggctgcag    1020
agggcccagg gccacaacaa cggcatctgc tggggcaacc agctgttcgt gaccgtggtg    1080
gacaccacca ggagcaccaa catgaccctg tgcaccgagg tgaccaagga gggcaccctac    1140 aagaacgaca acttcaagga gtacgtgagg cacgtggagg agtacgacct gcagttcgtg    1200
ttccagctgt gcaagatcac cctgaccgcc gagatcatga cctacatcca ccatggac     1260 agcaacatcc tggaggactg cagttcggc ctgacccccc ccccagcgc cagcctgcag    1320 gacacctaca ggttcgtgac cagccaggcc atcacctgcc agaagaccgc ccccccaag    1380 gagaaggagg accccctgaa caagtacacc ttctgggagg tgaacctgaa ggagaagttc    1440
agcgccgacc tggaccagtt ccccctgggc aggaagttcc tgctgcagag cggcctgaag    1500
gccaagccca ggctgaagag gagcgccccc accaccaggg cccccagcac caagaggaag    1560
aaggtgaaga agtga                                                     1575
```

```
<210> SEQ ID NO 9
<211> LENGTH: 1473
<212> TYPE: DNA
<213> ORGANISM: Artificial Sequence
<220> FEATURE:
<223> OTHER INFORMATION: coding sequence for truncated HPV58 L1 protein

<400> SEQUENCE: 9
atgaccgtgt acctgccccc cgtgcccgtg agcaaggtgg tgagcaccga cgagtacgtg        60
agcaggacca gcatctacta ctacgccggc agcagcaggc tgctggccgt gggcaacccc       120
tacttcagca tcaagagccc caacaacaac aagaaggtgc tggtgcccaa ggtgagcggc       180
ctgcagtaca gggtgttcag ggtgaggctg cccgacccca caagttcgg cttccccgac        240 accagcttct acaaccccga cacccagagg ctggtgtggg cctgcgtggg cctggagatc       300
ggcaggggcc agcccctggg cgtgggcgtg agcggccacc cctacctgaa caagttcgac       360
gacaccgaga ccagcaacag gtaccccgcc cagcccggca gcgacaacag ggagtgcctg       420
agcatggact acaagcagac ccagctgtgc ctgatcggct gcaagccccc caccggcgag       480
cactggggca agggcgtggc ctgcaacaac aacgccgccg ccaccgactg cccccccctg       540
gagctgttca acagcatcat cgaggacggc gacatggtgg acaccggctt cggctgcatg       600
gacttcggca ccctgcaggc caacaagagc gacgtgccca tcgacatctg caacagcacc       660
tgcaagtacc ccgactacct gaagatggcc agcgagcccc tacggcgacag cctgttcttc       720 ttcctgagga gggagcagat gttcgtgagg cacttcttca cagggccgg caagctgggc        780 gaggccgtgc ccgacgacct gtacatcaag ggcagcggca caccgccgt gatccagagc        840 agcgccttct cccccacccc cagcggcagc atcgtgacca gcgagagcca gctgttcaac       900 aagcccctact ggctgcagag ggcccagggc cacaacaacg gcatctgctg gggcaaccag      960
ctgttcgtga ccgtggtgga caccaccagg agcaccaaca tgaccctgtg caccgaggtg      1020
accaaggagg gcacctacaa gaacgacaac ttcaaggagt acgtgaggca cgtggaggag      1080
tacgacctgc agttcgtgtt ccagctgtgc aagatcaccc tgaccgccga gatcatgacc      1140
tacatccaca ccatggacag caacatcctg gaggactggc agttcggcct gaccccccc       1200 cccagcgcca gcctgcagga cacctacagg ttcgtgacca gccaggccat cacctgccag      1260
aagaccgccc cccccaagga gaaggaggac cccctgaaca agtacacctt ctgggaggtg      1320
aacctgaagg agaagttcag cgccgacctg gaccagttcc cctgggcag aagttcctg        1380 ctgcagagcg gcctgaaggc caagcccagg ctgaagagga gcgcccccac caccagggcc      1440
cccagcacca gaggaagaa ggtgaagaag taa                                    1473

<210> SEQ ID NO 10
<211> LENGTH: 1563
<212> TYPE: DNA
<213> ORGANISM: Artificial Sequence
<220> FEATURE:
<223> OTHER INFORMATION: coding sequence for truncated HPV58 L1 protein

<400> SEQUENCE: 10
atgtgctgca ccctggccat cctgttctgc gtggccgacg tgaacgtgtt ccacatcttc        60
ctgcagatga gcgtgtggag gcccagcgag gccaccgtgt acctgccccc cgtgcccgtg       120
agcaaggtgg tgagcaccga cgagtacgtg agcaggacca gcatctacta ctacgccggc       180
agcagcaggc tgctggccgt gggcaacccc tacttcagca tcaagagccc caacaacaac       240
aagaaggtgc tggtgcccaa ggtgagcggc ctgcagtaca gggtgttcag ggtgaggctg       300
```

```
cccgacccca caagttcgg cttccccgac accagcttct acaaccccga cacccagagg      360
ctggtgtggg cctgcgtggg cctggagatc ggcaggggcc agcccctggg cgtgggcgtg      420
agcggccacc cctacctgaa caagttcgac gacaccgaga ccagcaacag gtaccccgcc      480
cagcccggca gcgacaacag ggagtgcctg agcatggact acaagcagac ccagctgtgc      540
ctgatcggct gcaagccccc caccggcgag cactggggca agggcgtggc ctgcaacaac      600
aacgccgccg ccaccgactg cccccccctg gagctgttca acagcatcat cgaggacggc      660
gacatggtgg acaccggctt cggctgcatg gacttcggca ccctgcaggc caacaagagc      720
gacgtgccca tcgacatctg caacagcacc tgcaagtacc ccgactacct gaagatggcc      780
agcgagccct acggcgacag cctgttcttc ttcctgagga gggagcagat gttcgtgagg      840
cacttcttca cagggccgg caagctggg gaggccgtgc ccgacgacct gtacatcaag      900
ggcagcggca caccgccgt gatccagagc agcgccttct cccccacccc cagcggcagc      960
atcgtgacca gcgagagcca gctgttcaac aagcccctact ggctgcagag ggcccagggc     1020
cacaacaacg gcatctgctg gggcaaccag ctgttcgtga ccgtggtgga caccaccagg     1080
agcaccaaca tgacccctgtg caccgaggtg accaaggagg gcacctacaa gaacgacaac     1140
ttcaaggagt acgtgaggca cgtggaggag tacgacctgc agttcgtgtt ccagctgtgc     1200
aagatcaccc tgaccgccga gatcatgacc tacatccaca ccatggacag caacatcctg     1260
gaggactggc agttcggcct gacccccccc ccagcgcca gctgcagga cacctacagg     1320
ttcgtgacca gccaggccat cacctgccag aagaccgccc cccaaggaa gaaggagga   1380
cccctgaaca gtacacctt ctggggaggtg aacctgaagg agaagttcag cgccgacctg     1440
gaccagttcc ccctgggcag gaagttcctg ctgcagagcg gcctgaaggc caagcccagg     1500
ctgaagagga gcgcccccac caccagggcc cccagcacca gaggaagaa ggtgaagaag     1560
tga                                                              1563

<210> SEQ ID NO 11
<211> LENGTH: 1533
<212> TYPE: DNA
<213> ORGANISM: Artificial Sequence
<220> FEATURE:
<223> OTHER INFORMATION: coding sequence for truncated HPV58 L1 protein

<400> SEQUENCE: 11
atggccgacg tgaacgtgtt ccacatcttc ctgcagatga gcgtgtggag gcccagcgag       60
gccaccgtgt acctgccccc cgtgcccgtg agcaaggtgg tgagcaccga cgagtacgtg      120
agcaggacca gcatctacta ctacgccggc agcagcaggc tgctggccgt gggcaacccc      180
tacttcagca tcaagagccc caacaacaac aagaaggtgc tggtgcccaa ggtgagcggc      240
ctgcagtaca gggtgttcag ggtgaggctg cccgacccca caagttcgg cttccccgac      300
accagcttct acaaccccga cacccagagg ctggtgtggg cctgcgtggg cctggagatc      360
ggcaggggcc agcccctggg cgtgggcgtg agcggccacc cctacctgaa caagttcgac      420
gacaccgaga ccagcaacag gtaccccgcc cagcccggca gcgacaacag ggagtgcctg      480
agcatggact acaagcagac ccagctgtgc ctgatcggct gcaagccccc caccggcgag      540
cactggggca agggcgtggc ctgcaacaac aacgccgccg ccaccgactg cccccccctg      600
gagctgttca acagcatcat cgaggacggc gacatggtgg acaccggctt cggctgcatg      660
gacttcggca ccctgcaggc caacaagagc gacgtgccca tcgacatctg caacagcacc      720
tgcaagtacc ccgactacct gaagatggcc agcgagccct acggcgacag cctgttcttc      780
```

```
ttcctgagga gggagcagat gttcgtgagg cacttcttca acagggccgg caagctgggc    840
gaggccgtgc ccgacgacct gtacatcaag ggcagcggca acaccgccgt gatccagagc    900
agcgccttct tccccacccc cagcggcagc atcgtgacca gcgagagcca gctgttcaac    960
aagcccactc ggctgcagag ggcccagggc acaacaacga gcatctgctg gggcaaccag    1020
ctgttcgtga ccgtggtgga caccaccagg agcaccaaca tgaccctgtg caccgaggtg    1080
accaaggagg gcacctacaa gaacgacaac ttcaaggagt acgtgaggca cgtggaggag    1140
tacgacctgc agttcgtgtt ccagctgtgc aagatcaccc tgaccgccga gatcatgacc    1200
tacatccaca ccatggacag caacatcctg gaggactggc agttcggcct gacccccccc    1260
cccagcgcca gcctgcagga cacctacagg ttcgtgacca gccaggccat cacctgccag    1320
aagaccgccc cccccaagga gaaggaggac cccctgaaca agtacacctt ctgggaggtg    1380
aacctgaagg agaagttcag cgccgacctg gaccagttcc ccctgggcag gaagttcctg    1440
ctgcagagcg gcctgaaggc caagcccagg ctgaagagga gcgcccccac caccagggcc    1500
cccagcacca agaggaagaa ggtgaagaag tga                                 1533

<210> SEQ ID NO 12
<211> LENGTH: 1497
<212> TYPE: DNA
<213> ORGANISM: Artificial Sequence
<220> FEATURE:
<223> OTHER INFORMATION: coding sequence for truncated HPV58 L1 protein

<400> SEQUENCE: 12
atgagcgtgt ggaggcccag cgaggccacc gtgtacctgc cccccgtgcc cgtgagcaag    60
gtggtgagca ccgacgagta cgtgagcagg accagcatct actactacgc cggcagcagc    120
aggctgctgg ccgtgggcaa ccccctactt cagcatcaag gccccaacaa caacaagaag    180
gtgctggtgc ccaaggtgag cggcctgcag tacagggtgt tcagggtgag gctgcccgac    240
cccaacaagt tcggcttccc cgacaccagc ttctacaacc ccgacaccca gaggctggtg    300
tgggcctgcg tgggcctgga gatcggcagg ggccagcccc tgggcgtggg cgtgagcggc    360
caccccctacc tgaacaagtt cgacgacacc gagaccagca caggtaccc cgcccagccc    420
ggcagcgaca caggggagtg cctgagcatg gactacaagc agacccagct gtgcctgatc    480
ggctgcaagc cccccaccgg cgagcactgg ggcaaggggcg tggcctgcaa caacaacgcc    540
gccgccaccg actgcccccc cctggagctg ttcaacagca tcatcgagga cggcgacatg    600
gtggacaccg gcttcggctg catggacttc ggcaccctgc aggccaacaa gagcgacgtg    660
cccatcgaca tctgcaacag cacctgcaag taccccgact acctgaagat ggccagcgag    720
ccctacggca cagcctgtt cttcttcctg aggagggagc agatgttcgt gaggcacttc    780
ttcaacaggg ccggcaagct gggcgaggcc gtgcccgacg acctgtacat caagggcagc    840
ggcaacaccg ccgtgatcca gagcagcgcc ttcttcccca cccccagcgg cagcatcgtg    900
accagcgaga gccagctgtt caacaagccc tactggctgc agagggccca gggccacaac    960
aacggcatct gctggggcaa ccagctgttc gtgaccgtgg tggacaccac caggagcacc    1020
aacatgaccc tgtgcaccga ggtgaccaag gagggcacct acaagaacga caacttcaag    1080
gagtacgtga ggcacgtgga ggagtacgac ctgcagttcg tgttccagct gtgcaagatc    1140
accctgaccg ccgagatcat gacctacatc cacaccatgg acagcaacat cctggaggac    1200
tggcagttcg gcctgacccc ccccccagc gccagcctgc aggacaccta caggttcgtg    1260
```

```
accagccagg ccatcacctg ccagaagacc gccccccccca aggagaagga ggacccccctg    1320 aacaagtaca ccttctggga ggtgaacctg aaggagaagt tcagcgccga cctggaccag    1380
ttccccctgg gcaggaagtt cctgctgcag agcggcctga aggccaagcc caggctgaag    1440
aggagcgccc ccaccaccag ggcccccagc accaagagga gaaggtgaa gaagtga       1497
```

<210> SEQ ID NO 13
<211> LENGTH: 1458
<212> TYPE: DNA
<213> ORGANISM: Artificial Sequence
<220> FEATURE:
<223> OTHER INFORMATION: coding sequence for truncated HPV58 L1 protein

<400> SEQUENCE: 13

```
atgcccgtgc ccgtgagcaa ggtggtgagc accgacgagt acgtgagcag gaccagcatc      60
tactactacg ccggcagcag caggctgctg gccgtgggca ccccctactt cagcatcaag     120
agccccaaca caacaagaa ggtgctggtg cccaaggtga gcggcctgca gtacagggtg     180
ttcagggtga ggctgcccga ccccaacaag ttcggcttcc ccgacaccag cttctacaac     240
cccgacaccc agaggctggt gtgggcctgc gtgggcctgg agatcggcag gggccagccc     300
ctgggcgtgg gcgtgagcgg ccaccccctac ctgaacaagt cgacgacac cgagaccagc     360 aacaggtacc ccgcccagcc cggcagcgac aacagggagt gcctgagcat ggactacaag     420
cagacccagc tgtgcctgat cggctgcaag ccccccaccg cgagcactg gggcaagggc     480 gtggcctgca acaacaacgc cgccgccacc gactgccccc cctggagct gttcaacagc     540 atcatcgagg acggcgacat ggtggacacc ggcttcggct gcatggactt cggcacccctg     600 caggccaaca gagcgacgt gcccatcgac atctgcaaca gcacctgcaa gtaccccgac     660
tacctgaaga tggccagcga gccctacggc gacagcctgt tcttcttcct gaggagggag     720
cagatgttcg tgaggcactt cttcaacagg gccggcaagc tgggcgaggc cgtgcccgac     780
gacctgtaca tcaagggcag cggcaacacc gccgtgatcc agagcagcgc cttcttcccc     840 accccccagcg gcagcatcgt gaccagcgag agccagctgt caacaagcc ctactggctg     900 cagagggccc agggccacaa caacggcatc tgctgggggca accagctgtt cgtgaccgtg     960
gtggacacca ccaggagcac caacatgacc ctgtgcaccg aggtgaccaa ggagggcacc    1020
tacaagaacg acaacttcaa ggagtacgtg aggcacgtgg aggagtacga cctgcagttc    1080
gtgttccagc tgtgcaagat caccctgacc gccgagatca tgacctacat ccacaccatg    1140
gacagcaaca tcctggagga ctggcagttc ggcctgaccc cccccccag cgccagcctg    1200 caggacacct acaggttcgt gaccagccag gccatcacct gccagaagac cgccccccccc    1260 aaggagaagg aggaccccct gaacaagtac accttctggg aggtgaacct gaaggagaag    1320
ttcagcgccg acctggacca gttccccctg gcaggaagt tcctgctgca gagcggcctg    1380
aaggccaagc ccaggctgaa gaggagcgcc cccaccacca gggcccccag caccaagagg    1440
aagaaggtga agaagtaa                                                    1458
```

<210> SEQ ID NO 14
<211> LENGTH: 1398
<212> TYPE: DNA
<213> ORGANISM: Artificial Sequence
<220> FEATURE:
<223> OTHER INFORMATION: coding sequence for truncated HPV58 L1 protein

<400> SEQUENCE: 14

```
atgtactacg ccggcagcag caggctgctg gccgtgggca ccccctactt cagcatcaag      60
```

```
agccccaaca caacaagaa ggtgctggtg cccaaggtga gcggcctgca gtacagggtg        120
ttcagggtga ggctgcccga ccccaacaag ttcggcttcc ccgacaccag cttctacaac        180
cccgacaccc agaggctggt gtgggcctgc gtgggcctgg agatcggcag gggccagccc        240
ctgggcgtgg gcgtgagcgg ccaccccta ctgaacaagt tcgacgacac cgagaccagc         300
aacaggtacc ccgcccagcc cggcagcgac aacagggagt gcctgagcat ggactacaag        360
cagacccagc tgtgcctgat cggctgcaag ccccccaccg cgagcactg gggcaagggc         420 gtggcctgca caacaacgc cgccgccacc gactgccccc cctggagct gttcaacagc          480 atcatcgagg acggcgacat ggtggacacc ggcttcggct gcatggactt cggcaccctg        540
caggccaaca gagcgacgt gcccatcgac atctgcaaca gcacctgcaa gtaccccgac         600
tacctgaaga tggccagcga gccctacggc gacagcctgt tcttcttcct gaggagggag        660
cagatgttcg tgaggcactt cttcaacagg gccggcaagc tgggcgaggc cgtgcccgac        720
gacctgtaca tcaagggcag cggcaacacc gccgtgatcc agagcagcgc cttcttcccc        780 accccccagcg gcagcatcgt gaccagcgag agccagctgt caacaagcc ctactggctg        840 cagagggccc agggccacaa caacggcatc tgctggggca accagctgtt cgtgaccgtg        900
gtggacacca ccaggagcac caacatgacc ctgtgcaccg aggtgaccaa ggagggcacc        960
tacaagaacg acaacttcaa ggagtacgtg aggcacgtgg aggagtacga cctgcagttc        1020
gtgttccagc tgtgcaagat cacctgacc gccgagatca tgacctacat ccacaccatg        1080
gacagcaaca tcctggagga ctggcagttc ggcctgaccc cccccccag cgccagcctg        1140 caggacacct acaggttcgt gaccagccag gccatcacct gccagaagac cgccccccc        1200 aaggagaagg aggaccccct gaacaagtac accttctggg aggtgaacct gaaggagaag       1260
ttcagcgccg acctggacca gttccccctg ggcaggaagt tcctgctgca gagcggcctg       1320
aaggccaagc ccaggctgaa gaggagcgcc cccaccacca gggcccccag caccaagagg       1380
aagaaggtga agaagtga                                                     1398
```

<210> SEQ ID NO 15
<211> LENGTH: 1368
<212> TYPE: DNA
<213> ORGANISM: Artificial Sequence
<220> FEATURE:
<223> OTHER INFORMATION: coding sequence for truncated HPV58 L1 protein

<400> SEQUENCE: 15

```
atggtgggca ccccctactt cagcatcaag agccccaaca caacaagaa ggtgctggtg         60 cccaaggtga gcggcctgca gtacagggtg ttcagggtga ggctgcccga ccccaacaag       120
ttcggcttcc ccgacaccag cttctacaac cccgacaccc agaggctggt gtgggcctgc      180
gtgggcctgg agatcggcag gggccagccc ctgggcgtgg gcgtgagcgg ccaccccta      240 ctgaacaagt tcgacgacac cgagaccagc aacaggtacc ccgcccagcc cggcagcgac     300
aacagggagt gcctgagcat ggactacaag cagacccagc tgtgcctgat cggctgcaag     360
ccccccaccg cgagcactg gggcaagggc gtggcctgca caacaacgc cgccgccacc       420 gactgccccc cctggagct gttcaacagc atcatcgagg acggcgacat ggtggacacc      480
ggcttcggct gcatggactt cggcaccctg caggccaaca gagcgacgt gcccatcgac      540 atctgcaaca gcacctgcaa gtaccccgac tacctgaaga tggccagcga gccctacggc     600
gacagcctgt tcttcttcct gaggagggag cagatgttcg tgaggcactt cttcaacagg     660
```

```
gccggcaagc tgggcgaggc cgtgcccgac gacctgtaca tcaagggcag cggcaacacc    720
gccgtgatcc agagcagcgc cttcttcccc accccagcg gcagcatcgt gaccagcgag    780
agccagctgt tcaacaagcc ctactggctg cagagggccc agggccacaa caacggcatc    840
tgctggggca accagctgtt cgtgaccgtg gtggacacca ccaggagcac caacatgacc    900
ctgtgcaccg aggtgaccaa ggagggcacc tacaagaacg acaacttcaa ggagtacgtg    960
aggcacgtgg aggagtacga cctgcagttc gtgttccagc tgtgcaagat cacccctgacc   1020 gccgagatca tgacctacat ccacaccatg gacagcaaca tcctggagga ctggcagttc   1080
ggcctgaccc cccccccag cgccagcctg caggacacct acaggttcgt gaccagccag    1140
gccatcacct gccagaagac cgcccccccc aaggagaagg aggacccct gaacaagtac    1200 accttctggg aggtgaacct gaaggagaag ttcagcgccg acctggacca gttcccctg    1260 ggcaggaagt tcctgctgca gagcggcctg aaggccaagc ccaggctgaa gaggagcgcc    1320
cccaccacca gggcccccag caccaagagg aagaaggtga agaagtga             1368

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
catatgaccg tgtacctgcc c                                                21

<210> SEQ ID NO 17
<211> LENGTH: 26
<212> TYPE: DNA
<213> ORGANISM: Artificial Sequence
<220> FEATURE:
<223> OTHER INFORMATION: primer

<400> SEQUENCE: 17
gtcgacttac ttcttcacct tcttcc                                           26
```

TRUNCATED L1 PROTEIN OF HUMAN PAPILLOMAVIRUS TYPE 58

This application incorporates by reference the contents of a 45.8kb text file created on Jan. 21, 2016 and named "substituesequencelisting.txt," which is the sequence listing for this application.

FIELD OF THE INVENTION

The invention relates to the field of molecular virology and immunology. In particular, the invention relates to a truncated L1 protein of Human Papillomavirus Type 58, its coding sequence and preparation method, and a virus-like particle comprising the protein, wherein the protein and the virus-like particle are useful for preventing HPV (particularly HPV58) infection, and a disease caused by HPV (particularly HPV58) infection, such as cervical cancer. The invention also relates to the use of the protein and the virus-like particle in the preparation of a pharmaceutical composition or a vaccine for preventing HPV (particularly HPV58) infection, and a disease caused by HPV (particularly HPV58) infection, such as cervical cancer.

BACKGROUND OF THE INVENTION

Human Papillomavirus (HPV), a non-enveloped, deoxyribonucleic acid (DNA) virus, belongs to the family Papillomaviridae. The viral genome is a double-stranded, closed circular DNA, which is approximately 7.2-8 kb in length and contains 8 open reading frames (ORFs). The genome can be divided into three parts in terms of function: (1) the early region (E), approximately 4.5 Kb in length, coding for 6 non-structural proteins E1, E2, E4-E7 associated with virus replication, transcription and transformation; (2) the late region (L), approximately 2.5 Kb in length, coding for the major capsid protein L1 and the minor capsid protein L2; (3) the long control region (LCR), located between the end of the L region and the initiating terminal of the E region, approximately 800-900 by in length, and comprising regulator elements for DNA replication and expression instead of coding for proteins. HPV viral particles have a diameter of 45-55 nm, wherein the nucleocapsid, consisting of L1 and L2, exhibits icosahedral symmetry and comprises 72 capsomers.

Currently, there are over 100 different types of HPV, mainly causing papillary disease in the skin and mucosa of human. HPV types are divided into three groups depending on their relation with tumorigenesis: (1) group of low or no cancerogenic risk, containing HPV 6, 11, 39, 41, 42, and 43; (2) group of medium cancerogenic risk, containing HPV 31, 33, 35, 51 and 52; and (3) group of high cancerogenic risk, containing HPV 16, 18, 58, and 45.

HPV molecular epidemiological investigation demonstrates that infection by high-risk HPV types is an important factor responsible for the development of cervical cancer. Among all the cervical cancer specimens, HPV DNA is detected in over 80% of them. Cervical cancer is a common malignant tumor among women, the incidence of which is only next to breast cancer, and seriously threatens the health of women. There are about 490,000 newly reported cases worldwide every year, and nearly 270,000 people die of this disease annually (Boyle, P., and J. Ferlay. Ann Oncol 2005, 16:481-8). Cases in developing countries account for approximately 83% of the total cervical cancer cases. In these developing countries, the cervical cancer cases account for about 15% of female malignant tumors, in contrast to 1.5% in developed countries. Cervical cancer is most prevalent in sub-Saharan Africa, central and Southern Asia, Latin America, and Eastern Asia. Cervical cancer is also prevalent in China. The incidence of cervical cancer among married women is as high as 1026/100000 in Lueyang County of Shanxi Province.

Meta-analysis of the distribution of HPV types in the worldwide cervical cancer specimens shows that the most common HPV types found in cervical cancer specimens are HPV 16, 18, 45, 31, 33, 58, 52, 35, 59, 56, 6, 51, 68, 39, 82, 73, 66 and 70 (listed in descending order, Clifford G M, Smith J S, Plummer M, et al. Br J Cancer, 2003, 88(1): 63-73).

However, the distribution of HPV types exhibits some characteristics of geographical distribution and populations. In particular, the infection rate of HPV58 in Asia is higher than that in developed countries such as in European and America. Recently, an investigation on the HPV types infected in Chinese women shows that among cervical cancer patients, the infection rate of HPV58 is 7.2%, preceded only by HPV16 (58.7%) and HPV18 (11.0%), and among women with high-grade squamous epithelial lesion or low-grade squamous epithelial lesion and normal women, the infection rate of HPV58 is preceded only by HPV16 (Y P Bao, N L1, J S Smith and Y L Qiao. International Journal of STD & AIDS, 2008, 19: 106-111). This suggests that the infection rate of HPV58 in Chinese women is higher than the worldwide level, and that HPV58 is a HPV type to which Chinese women and Asian women are generally susceptible.

Currently, the commercially available HPV vaccines are GARDASIL® from Merck and CERVARIX® from GSK, which comprise HPV6/11/16/18 and HPV16/18 VLP, respectively, but do not comprise HPV type 58 to which Chinese women and Asian women are generally susceptible.

Therefore, HPV vaccines which are safe and effective for women in developing countries such as in China and Asia, in particular, those directed to high-risk type such as HPV 16, 18 and 58, are effective means for effectively preventing cervical cancer and improving the health condition of women, in particular the health condition of Chinese and Asian women.

HPV L1 protein, with a molecular weight of 55-60 kDa, is the major capsid protein of the human papillomavirus and the main target protein of the HPV vaccine. HPV L1 protein expressed in many expression systems can form Virus-Like Particles (VLPs) which resemble native HPV particles morphologically, without the assistance of the L2 protein. The VLPs, consisting of 72 pentamers of the L1 proteins, exhibit icosahedral symmetry. Since the VLPs retain the native epitopes of the viral particles, they are highly immunogenic and can induce the generation of neutralization antibodies against homologous HPV (Kirnbauer, R., F. Booy, et al. 1992 Proc Natl Acad Sci USA 89(24): 12180-4). Furthermore, the VLPs are safe and have no potential cancergenic risk as they contain no viral nucleic acids. Therefore, VLP vaccines have become the primary candidate for HPV vaccines.

The key for development of HPV VLP vaccines lies in efficient production of VLP samples in large-scale. Currently, the most common expression systems used for VLP are divided into eukaryotic expression systems and prokaryotic expression systems.

The commonly used eukaryotic expression systems comprise poxvirus, insect baculovirus and yeast expression systems. HPV L1 protein expressed in eukaryotic expression systems shows little conformational difference from that of the native virus, and can self-assemble into VLPs. Thus, purified VLPs can be easily obtained after simple gradient density centrifugation. It brings a lot of convenience to the purification work. However, due to the high culture costs and low expression level of eukaryotic expression systems, it is quite difficult to product industrially on a large-scale. The HPV vaccine GARDASIL®, which came into the market recently, is more expensive than others due to low expression level and high production cost of the *Saccharomyces cerevisiae* expression system employed in its manufacture, and therefore, its general application is limited.

The expression of HPV L1 protein in a prokaryotic expression system such as *E. coli* expression system has been previously reported. The expression of HPV 16 L1 protein by employing *E. coli* has been reported (Banks, L., G. Matlashewski, et al. (1987). J Gen Virol 68 (Pt 12); 3081-9). However, most HPV L1 proteins expressed in *E. coli* lose their native conformation and cannot induce protective antibodies against HPV. Alternatively, although HPV VLPs can be obtained from the proteins by steps such as purification from inclusion bodies and renaturation (Kelsall, S. R. and J. K. Kulski (1995). J Virol Methods 53(1): 75-90), it is difficult to apply this method to large-scale production, as the proteins are largely lost during the renaturation process and the yield is low. Although HPV L1 protein may be expressed in a soluble form with a correct conformation in *E. coli* and be dissolved in the supernatants of *E. coli* lysate, the expression level is low. Moreover, since there are large number and amounts of impure proteins, it is difficult to isolate the proteins of interest from them. Although it is also reported that the expression level of L1 protein can be increased in the supernatants by means of GST fusion expression and the purification of the protein of interest is facilitated (L1, M., T. P. Cripe, et al. (1997), J Virol 71(4): 2988-95), it still cannot be applied to larger-scale production because expensive enzymes are required to cleave the fusion protein.

Therefore, the obtainment of a HPV L1 protein capable of inducing the generation of protective antibodies against HPV, and a virus-like particle consisting of the same, at low cost, are still urgent in the art, in order to make the large-scale industrial production of vaccines for cervical cancer possible.

DESCRIPTION OF THE INVENTION

The invention is at least partially based on the inventors' surprised discovery: a truncated HPV58 L1 protein capable of inducing the generation of neutralization antibodies against HPV58 can be expressed in an *E. coli* expression system on a large scale, wherein the truncated HPV58 L1 protein can be produced with a high yield, and the purity of the purified protein reaches at least 50% or higher (such as 60%, 70%, 80%, 90%, 95%, 96%, 97%, 98%, and 99%). Moreover, further treatment of the purified protein results in the obtainment of VLPs capable of inducing the generation of protective antibodies against HPV58.

Therefore, in one aspect, the invention relates to a truncated HPV58 L1 protein or variants thereof, wherein said protein has 5-70 amino acids, for example, 5-60, 15-60, 20-50, 30-45, 35-40 amino acids, such as 5, 15, 27, 35, 40, 60 or 70 amino acids, truncated at its N-terminal.

In one aspect, the invention relates to a truncated HPV58 L1 protein or variants thereof, wherein said protein has 5-70 amino acids, for example, 5-60, 15-60, 20-50, 30-45, 35-40 amino acids, such as 5, 15, 27, 35, 40, 60 or 70 amino acids, truncated at its N-terminal, as compared with wild type HPV58 L1 protein.

In a preferred embodiment, the truncated HPV58 L1 protein has 5-70 amino acids, such as 5, 15, 27, 35, 40, 60 or 70 amino acids, truncated at its N-terminal, as compared with wild type HPV58 L1 protein. In another preferred embodiment, the truncated HPV58 L1 protein has 35 amino acids truncated at its N-terminal, as compared with wild type HPV58 L1 protein.

In another preferred embodiment, the truncated HPV58 L1 protein (cited hereafter as the truncated protein) has an amino acid sequence as set forth in SEQ ID NO: 1, SEQ ID NO: 2, SEQ ID NO: 3, SEQ ID NO: 4, SEQ ID NO: 5, SEQ ID NO: 6, or SEQ ID NO: 7. In another preferred embodiment, the truncated protein has an amino acid sequence as set forth in SEQ ID NO: 1.

In another aspect, the invention relates to a polynucleotide encoding the truncated protein or variants thereof according to the invention, and a vector containing the polynucleotide.

Vectors for inserting a polynucleotide of interest are well known in the art, including, but not limited to clone vectors and expression vectors. In one embodiment, the vectors are, for example, plasmids, phages, cosmids, etc.

In another aspect, the invention also relates to a host cell comprising the polynucleotide or vector. The host cell includes, but is not limited to prokaryotic cells such as *E. coli* cells, and eukaryotic cells such as yeast cells, insect cells, plant cells and animal cells (such as mammalian cells, for example, mouse cells, human cells, etc.). The host cell according to the invention may also be a cell line, such as 293T cell.

In another aspect, the invention relates to a HPV58 virus-like particle, comprising or consisting of the truncated protein or variants thereof according to the invention.

In one preferred embodiment, the HPV58 virus-like particle according to invention comprises or is consisted of or formed from the truncated HPV58 L1 protein having 5-70 amino acids, for example, 5-60, 15-60, 20-50, 30-45, 35-40 amino acids, such as 5, 15, 27, 35, 40, 60 or 70 amino acids, truncated at its N-terminal, as compared with wild type HPV58 L1 protein. In a particularly preferred embodiment, the HPV58 virus-like particle according to invention comprises or is consisted of or formed from the truncated HPV58 L1 protein having a sequence as set forth in SEQ ID NO: 1, SEQ ID NO: 2, SEQ ID NO: 3, SEQ ID NO: 4, SEQ ID NO: 5, SEQ ID NO: 6, or SEQ ID NO: 7.

In another aspect, the invention also relates to a composition comprising said truncated protein or variants thereof, or said polynucleotide or vector or host cell or HPV58 virus-like particle. In one preferred embodiment, the composition comprises the truncated protein or variants thereof according to the invention. In another preferred embodiment, the composition comprises the HPV58 virus-like particle according to the invention.

In another aspect, the invention also relates to a pharmaceutical composition or vaccine comprising the HPV58 virus-like particle according to invention, and optionally pharmaceutically acceptable carriers and/or excipients. The pharmaceutical composition or vaccine according to the invention is useful for preventing HPV (particularly HPV58) infection, and a disease caused by HPV (particularly HPV58) infection, such as cervical cancer.

In one preferred embodiment, the HPV58 virus-like particle is present at an amount effective for preventing HPV infection or cervical cancer. In another preferred embodiment, the pharmaceutical composition or vaccine according to the invention further comprises at least one virus-like particle selected from the group consisting of HPV6 L1 protein virus-like particle, HPV11 L1 protein virus-like particle, HPV16 L1 protein virus-like particle, HPV18 L1 protein virus-like particle, HPV31 L1 protein virus-like particle, HPV33 L1 protein virus-like particle, HPV45 L1 protein virus-like particle, and HPV52 L1 protein virus-like particle;

preferably these virus-like particles are independently present at an amount effective for preventing cervical cancer or infection by the corresponding HPV subtype.

The pharmaceutical composition or vaccine according to the invention may be administrated by methods well known in the art, for example, but not limited to, orally or by injection. In the invention, the particularly preferred administration route is injection.

In one preferred embodiment, the pharmaceutical composition or vaccine according to the invention is administrated in a form of a unit dosage. For example, but not for limiting the invention, each unit dosage contains 5 µg-80 µg, preferably 20 µg-40 µg HPV58 virus-like particle.

In another aspect, the invention relates to a method for obtaining the truncated protein according to the invention, comprising expressing the truncated protein according to the invention with an *E. coli* expression system, and carrying out a purification process on the lysis supernatant containing the truncated protein.

In a preferred embodiment, the method for obtaining the truncated protein according to the invention comprises, a) expressing the truncated protein in *E. coli*;

b) disrupting the *E. coli*, which has expressed the truncated protein, in a solution at a salt concentration of 100 mM to 600 mM, and isolating the supernatant;

c) decreasing the salt concentration of the supernatant of b) to 100 mM or less, by using water or a solution at a low salt concentration, lowest to 0, and collecting a precipitate;

d) re-dissolving the precipitate of c) in a solution at a salt concentration of 150 mM to 2500 mM, and adding a reductant to the solution, and then isolating the resultant solution, wherein the resultant solution contains the truncated HPV58 L1 protein with a purity of at least 50%.

In one embodiment of the invention, the salt concentration in b) is from 200 mM to 500 mM.

More generally, the invention also relates to a method for obtaining HPV L1 protein, such as the truncated protein according to the invention, comprising, a) expressing HPV L1 gene encoding HPV L1 protein in *E. coli*;

b) disrupting the *E. coli*, which has expressed the HPV L1 protein, in a solution at a salt concentration of 100 mM to 600 mM, and isolating the supernatant;

c) decreasing the salt concentration of the supernatant of b) to 100 mM or less, by using water or a solution at a low salt concentration, lowest to 0, and collecting a precipitate;

d) re-dissolving the precipitate of c) in a solution at a salt concentration of 150 mM to 2500 mM, and adding a reductant to the solution, and then isolating the resultant solution, wherein the resultant solution contains the HPV L1 protein with a purity of at least 50%.

The invention also relates to a method for obtaining the HPV58 virus-like particle according to invention, on the basis of the obtainment of the truncated protein of the invention as described above, comprising the steps of:

e) further purifying the truncated HPV58 L1 protein according to the invention with a purity of at least 50% by a chromatography; and f) removing the reductant from the truncated protein obtained in e).

The invention also relates to a method for preparing a vaccine, comprising blending the HPV58 virus-like particle according to the invention, and optionally, one or more virus-like particles selected from the group consisting of virus-like particles of HPV types 6, 11, 16, 18, 31, 33, 45 and 52, with pharmaceutically acceptable carriers and/or excipients. As described above, the vaccine obtained is useful for preventing HPV (particularly HPV58) infection, and a disease caused by HPV (particularly HPV58) infection, such as cervical cancer.

In another aspect, the invention relates to a method for preventing HPV infection or a disease caused by HPV infection, comprising administrating to a subject a prophylactically effective amount of the HPV58 virus-like particle or pharmaceutical composition or vaccine according to the invention. In one preferred embodiment, the HPV infection is HPV58 infection. In another preferred embodiment, the disease caused by HPV infection includes, but is not limited to cervical cancer. In another preferred embodiment, the subject is mammalian, such as human.

In another aspect, the invention also relates to the use of the truncated protein or variants thereof or the HPV58 virus-like particle according to invention in the preparation of a pharmaceutical composition or vaccine for preventing HPV infection or a disease caused by HPV infection. In one preferred embodiment, the HPV infection is HPV58 infection. In another preferred embodiment, the disease caused by HPV infection includes, but is not limited to cervical cancer.

In another aspect, the invention also relates to the truncated protein or variants thereof or the HPV58 virus-like particle according to invention, for use in the prevention of HPV infection or a disease caused by HPV infection. In one preferred embodiment, the HPV infection is HPV58 infection. In another preferred embodiment, the disease caused by HPV infection includes, but is not limited to cervical cancer.

Definitions of the Term in the Present Invention

In the invention, unless otherwise specified, the scientific and technical terms used herein have the meanings as generally understood by a person skilled in the art. Moreover, the laboratory operations of cell culture, molecular genetics, nucleic acid chemistry, and immunology used herein are the routine operations widely used in the corresponding fields. Meanwhile, in order to better understand the invention, the definitions and explanations of the relevant terms are provided as follows.

According to the invention, the term "a protein having X amino acids truncated at its N-terminal" refers to a protein resulted from substituting the amino acid residues from positions 1 to X at the N-terminal of the protein with methionine residue encoded by an initiator codon (for initiating protein translation). For example, a HPV58 L1 protein having 35 amino acids truncated at its N-terminal refers to a protein resulted from substituting the amino acid residues from positions 1 to 35 at the N-terminal of wild type HPV58 L1 protein with methionine residue encoded by an initiator codon.

According to the invention, the term "variant" refers to a protein, whose amino acid sequence is different from the truncated HPV58 L1 protein according to the invention (for example, the protein as set forth in SEQ ID NO: 1 or SEQ ID NO: 2) by one or more (for example, 1-10, or 1-5 or 1-3) amino acids (such as conservative amino acid substitutions), or which has an identity of at least 60%, 80%, 85%, 90%, 95%, 96%, 97%, 98%, or 99% to the truncated HPV58 L1 protein according to the invention (for example, the protein as set forth in SEQ ID NO: 1 or SEQ ID NO: 2), and which retains the essential characteristics of the truncated protein. The term "essential characteristics" may be one or more of the following characteristics: capable of inducing the generation of neutralization antibodies against HPV58; capable of being expressed in *E. coli* in a soluble manner; capable of obtaining purified protein with a high yield by the expression and purification methods as involved in the invention.

According to the invention, the term "identity" refers to the match degree between two polypeptides or between two nucleic acids. When two sequences for comparison have the same base or amino acid monomer sub-unit at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by using a computer program such as Align program (DNAstar, Inc.) which is based on the method of Needleman, et al. (J. Mol. Biol. 48:443-453, 1970). The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

As used in the invention, the term "conservative substitution" refers to amino acid substitutions which would not negatively affect or change the biological activity of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue similar to the corresponding amino acid residue physically or functionally (such as, having similar size, shape, charges, chemical properties including the capability of forming covalent bond or hydrogen bond, etc.). The families of amino acid residues having similar side chains have been defined in the art. These families include amino acids having alkaline side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having β-branched side chains (such as threonine, valine, isoleucine) and amino acids having aromatic side chains (for example, tyrosine, phenylalanine, tryptophan, histidine). Therefore, a corresponding amino acid residue is preferably substituted with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl. Acad. Set USA 94: 412-417 (1997), which are incorporated herein by reference).

According to the invention, the term "E. coli expression system" refers to an expression system consisting of E. coli (strain) and a vector, wherein the E. coli (strain) includes, but are not limited to: G1698, ER2566, BL21 (DE3), B834 (DE3), BLR (DE3), etc., which are available on the market.

According to the invention, the term "vector" refers to a nucleic acid vehicle which can have a polynucleotide inserted therein. When the vector allows for the expression of the protein encoded by the polynucleotide inserted therein, the vector is called an expression vector. The vector can have the carried genetic material elements expressed in a host cell by transformation, transduction, and transfection into the host cell. Vectors are well known by a person skilled in the art, including, but not limited to plasmids, phages, cosmids and the like.

According to the invention, the term "a truncated HPV58 L1 protein" refers to the protein with one or more amino acids deleted at the N- and/or C-terminal of wild-type HPV58 L1 protein, wherein the example of the wild-type HPV58 L1 protein includes, but is not limited to, the full-length L1 proteins such as ACJ13480, ACX32376.1 or ACK37663.1 in NCBI database.

According to the invention, the term "a gene fragment of a truncated HPV58 L1 protein" refers to the gene fragments with the nucleotide(s) encoding one or more amino acids deleted at 5' or 3' terminal of the wild-type HPV58 L1 gene, wherein the full-length gene sequence of the wild-type HPV58 L1 gene includes, but is not limited to, the following sequences: AY101598.2, D90400.1, FJ407208.1, FJ615305.1 and FN178626.1 in NCBI database.

According to the invention, the term "pharmaceutically acceptable carriers and/or excipients" refers to carriers and/or excipients that are pharmacologically and/or physiologically compatible with subjects and active ingredients, and are well known in the art (see, for example, Remington's Pharmaceutical Sciences. Edited by Gennaro A R, 19th ed. Pennsylvania: Mack Publishing Company, 1995), including, but not limited to pH adjusting agents, surfactants, adjuvants, and ionic strength enhancers. For example, pH adjusting agents include, but are not limited to, phosphate buffers; surfactants include, but are not limited to: anion surfactants, cation surfactants, or non-ionic surfactants (for example, Tween-80®); adjuvants include, but are not limited to, aluminum adjuvants (for example, aluminum hydroxide) and Freund's adjuvants (for example, Freund's complete adjuvant); and ionic strength enhancers include, but are not limited to, NaCl.

According to the invention, the term "an effective amount" refers to an amount that can effectively achieve the intended purpose. For example, an amount effective for preventing a disease (such as HPV infection) refers to an amount effective for preventing, suppressing, or delaying the occurrence of a disease (such as HPV infection). The determination of such an effective amount is within the ability of a person skilled in the art.

According to the invention, the term "chromatography" includes, but is not limited to: ion exchange chromatography (e.g. cation-exchange chromatography), hydrophobic interaction chromatography, absorbent chromatography (e.g. hydroxyapatite chromatography), gel filtration chromatography (gel exclusion chromatography), and affinity chromatography.

According to the invention, the truncated HPV58 L1 proteins according to the invention may be obtained preferably by the following steps:

disrupting E. coli, which expresses a truncated HPV58 L1 protein, in a buffer at a salt concentration of 100-600 mM, preferably 200-500 mM, and centrifuging the disrupted solution to obtain a supernatant;

precipitating the truncated HPV58 L1 protein from the supernatant by decreasing the salt concentration of the resultant supernatant to 100 mM-0 mM with water or a low-salt solution (generally, with a salt concentration lower than the one of the buffer for disrupting);

re-dissolving the precipitate in a solution containing a reductant and having a salt concentration of 150-2500 mM, preferably greater than 200 mM, resulting in a solution comprising the truncated HPV58 L1 proteins with a purity of at least 50%, preferably at least 70%, more preferably at least 80%.

The buffers used in the methods of the invention are well known in the art, including, but not limited to Tris buffers, phosphate buffers, HEPES buffers, MOPS buffers, etc.

According to the invention, the disrupting of the host cell can be accomplished by methods well known by a person skilled in the art, including, but not limited to homogenizer disrupting, ultrasonic treatment, grinding, high pressure extrusion, lysozyme treatment, etc.

The salts used in the methods of the invention include, but are not limited to: one or more of acidic salts, basic salts, neutral salts, for example, alkali metal salts, alkaline-earth metal salts, ammonium salts, hydrochlorides, sulfates, bicarbonates, phosphate salts or biphosphates, especially NaCl, KCl, $NH_4Cl$, $(NH_4)_2SO_4$. NaCl is particularly preferred. The reductant used in the methods of the invention includes, but is not limited to, DTT and 2-mercaptoethanol, at an amount including, but not limited to, 10-100 mM.

According to the invention, the HPV58 VLPs according to the invention may be produced by the following steps: further purifying the truncated HPV58 L1 protein with a purity of at least 50% as described above by e.g. a chromatography, and thereby obtaining a purified truncated protein solution; and removing the reductant from the solution to obtain the HPV58 VLPs. Methods for removing the reductant are known in the art, including, but not limited to, dialysis, ultrafiltration, and chromatography.

Beneficial Effect

Presently, the expression systems useful for preparing HPV VLPs include eukaryotic and prokaryotic expression systems.

HPV L1 proteins expressed in eukaryotic expression systems show little conformational difference from that of the native virus, and can self-assemble into VLPs. In most cases, VLPs with a correct conformation can be obtained by simple purification. Nevertheless, eukaryotic expression systems, such as the baculovirus and yeast expression systems, are difficult to be applied to large-scale industrial production due to shortcomings such as low expression levels and high culturing costs.

Prokaryotic expression systems, such as *E. coli* systems, have the advantages of high expression levels and low culturing costs. However, when expressed in *E. coli* system, HPV L1 proteins usually lose their native conformations and are expressed in a form of inclusion bodies in the precipitant. Currently, renaturation of the protein from inclusion bodies is still a challenge worldwide. Due to the difficulty and inefficiency of renaturation, this method is limited to small-scale lab research and cannot be applied to the large-scale obtainment of VLPs with a correct conformation from the inclusive bodies. Although HPV L1 protein may be expressed in a soluble form with a correct conformation in *E. coli*, their expression levels are low. Moreover, it is quite difficult to purify the HPV L1 proteins from the numerous soluble proteins in the *E. coli* lysate supernatant. Generally, the purification is carried out by means such as fusion expression and affinity chromatography which are not feasible for industrial-scale processes due to expensive enzymes employed therein.

The N-truncated HPV58 L1 protein and the method for preparing the same, as provided in the invention, effectively solve the problem. Firstly, *E. coli* expression systems are used in the invention to express the N-truncated HPV58 L1 protein, which ensures a high expression level. Secondly, the truncated protein is selectively precipitated from the *E. coli* lysate supernatant under mild conditions. The truncated protein is then redissolved in a salt buffer to significantly improve its purity while still retaining its correct conformation. The truncated protein solution thus obtained can be further purified directly by chromatography such as ion-exchange and hydrophobic exchange chromatography so as to obtain the protein of interest with a high purity (such as a purity up to 80%). Further, the purified, truncated protein obtained from these steps, can self-assemble into VLP with good immunogenicity and the ability to induce neutralization antibodies of a high titer against HPV58, which is a good vaccine for preventing HPV58 infection in human.

Therefore, the invention has the following advantages. The truncated protein of the invention can be expressed in *E. coli* expression systems on a large scale whilst retaining the antigenicity, immunogenicity, and particle self-assembly ability of the full-length HPV58 L1 protein. Expensive enzymes are not required in the preparation methods used in the invention, i.e. the cost is low. Furthermore, since the truncated protein is not subjected to the intensive procedures of denaturation and renaturation during purification, the loss of the protein is low and the yield is high. The VLPs formed from the truncated protein can induce the generation of protective antibodies against HPV at a high titer and can be applied to the preparation of vaccines. Thus, the truncated protein of the invention and the preparation method thereof can be applied to large-scale industrial production, and makes the large-scale industrial production of vaccines for cervical cancer possible.

The embodiments of the invention are further described in detail by reference to the drawings and examples. However, a person skilled in the art would understand that the following drawings and examples are intended for illustrating the invention only, rather than defining the scope of the invention. According to the detailed description of the following drawings and preferred embodiments, various purposes and advantages of the invention are apparent for a person skilled in the art.

μL); Lane 5: elution fraction eluted with 1000 mmol/L NaCl (the loading volume was 20 μL). The result showed that after purification with CHT-II, HPV58N35C-L1 protein eluted with 1000 mmol/L NaCl reached a purity of about 98%.

Figure 3:
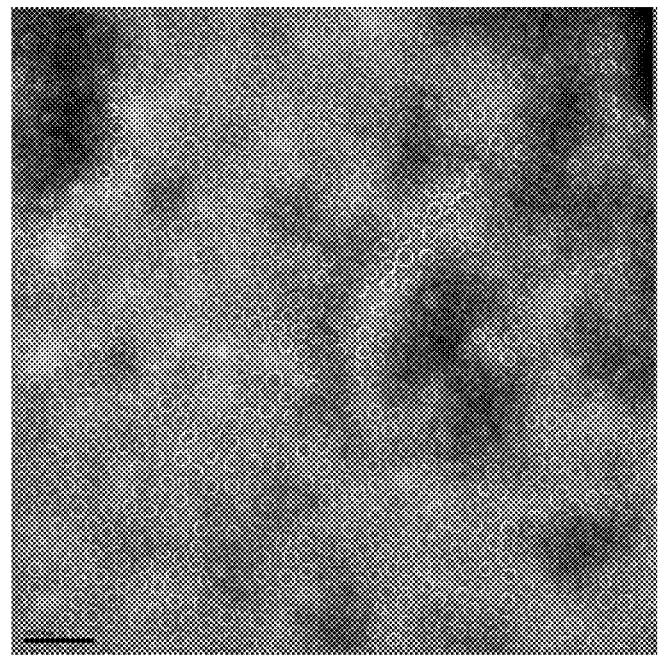

FIG. 3 shows the transmission electron microscopy (TEM) photograph of HPV58N35C-L1 VLPs obtained in Example 4 (taken at 50,000× magnification, Bar=0.2 μm). A large number of VLPs with a radius of about 25 nm were observed in visual field, wherein the particle size was consistent with the theoretic size and the particles were homogenous.

Figure 4:
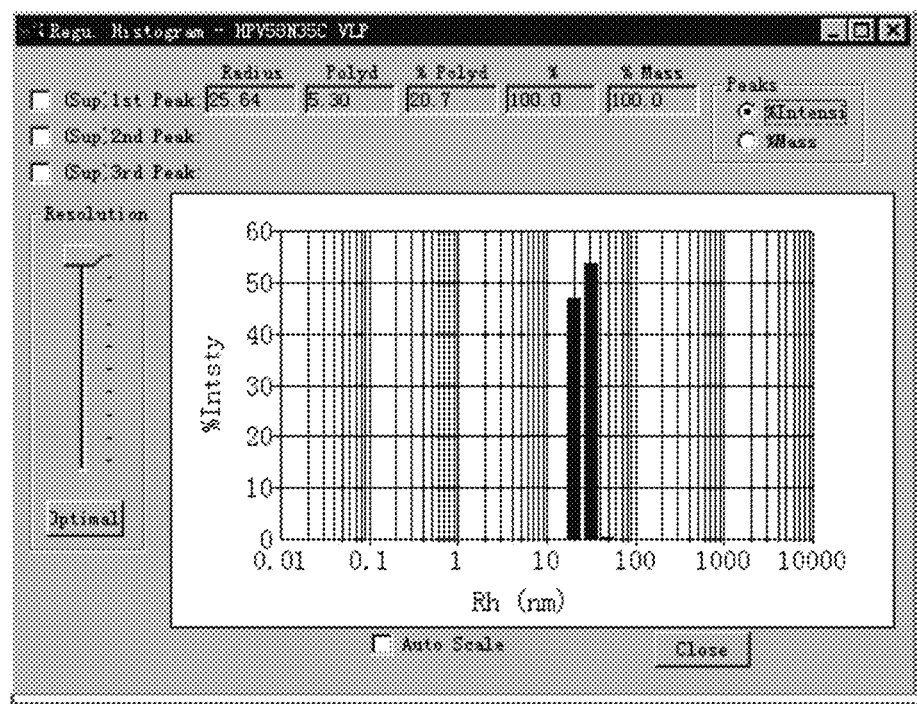

FIG. 4 shows the dynamic light-scattering measurement result of HPV58N35C-L1 VLPs obtained in Example 4. The result showed that HPV58N35C-L1 VLPs had a hydrodynamic radius of 25.64 nm and a particle assembly rate of 100%.

Figure 5:
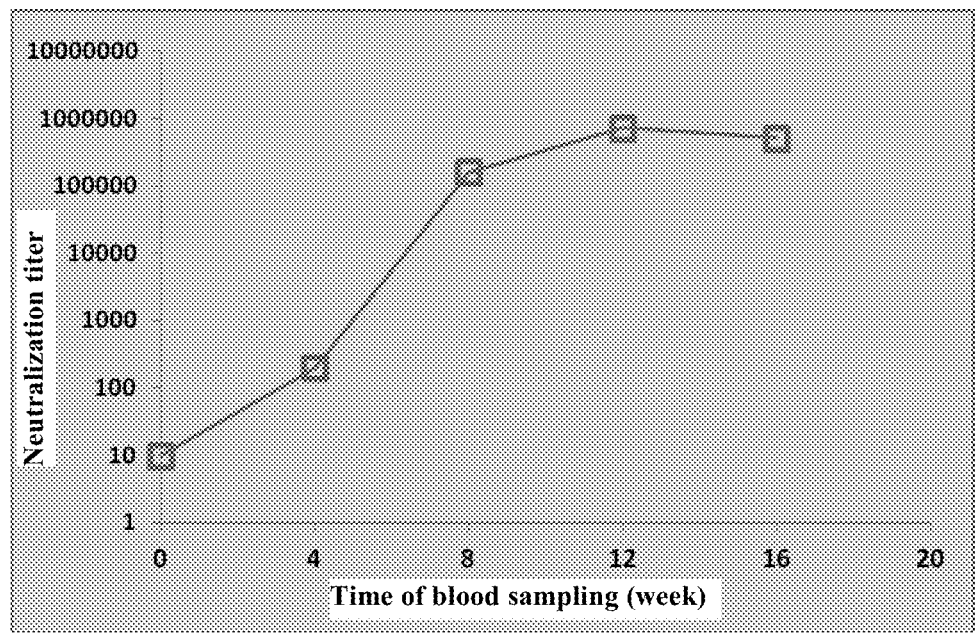

FIG. 5 shows neutralization titers of antibodies in serum at different stages after vaccination of rabbits with HPV58N35C-L1 VLPs as determined in Example 5. The neutralization titers of antibodies increased significantly 2 months after the first vaccination, and reached a peak level of $10^5$ after a booster. The longitudinal axis represents the neutralization titers of antibodies; the horizontal axis represents the time of blood sampling.

Figure 6:
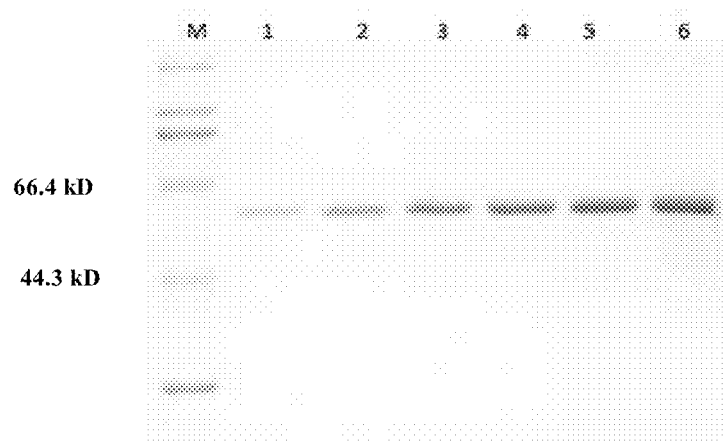
Figure 7A:
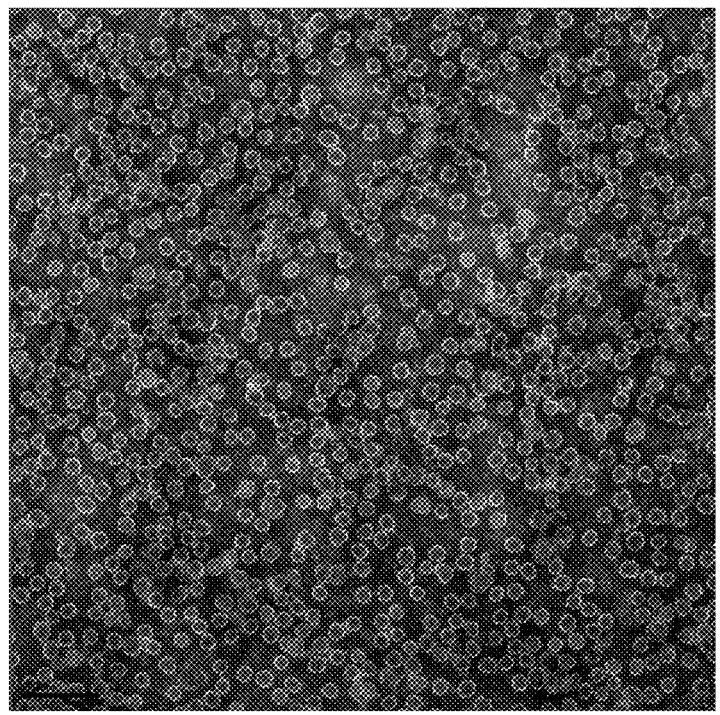
Figure 7B:
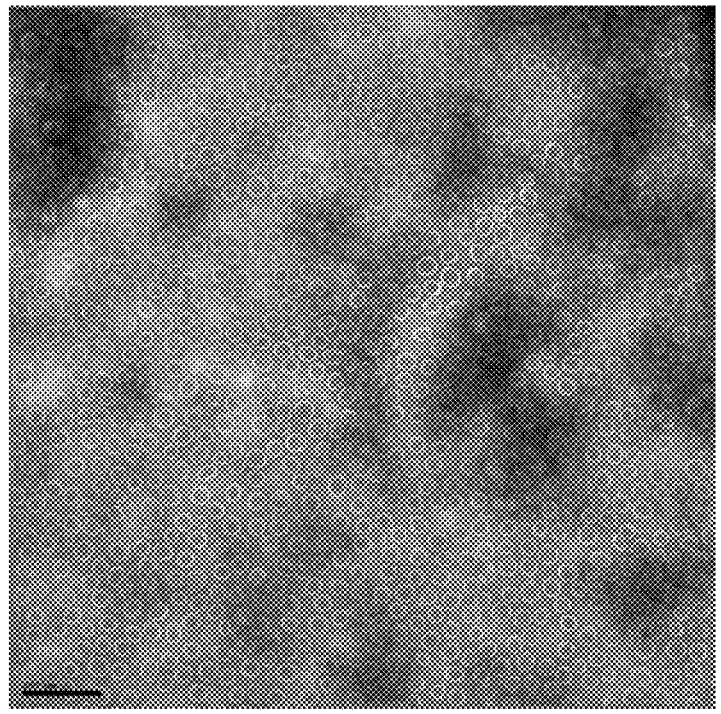
Figure 7C:
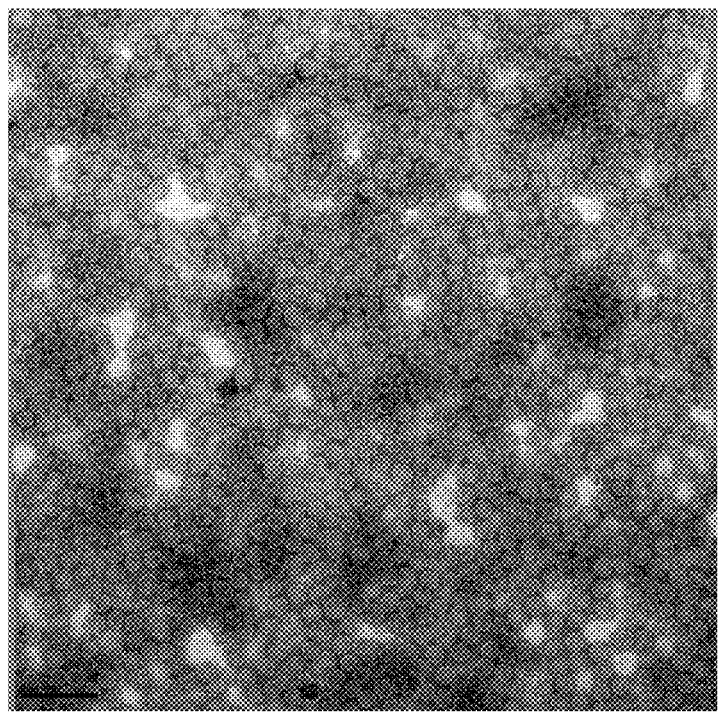
Figure 7D:
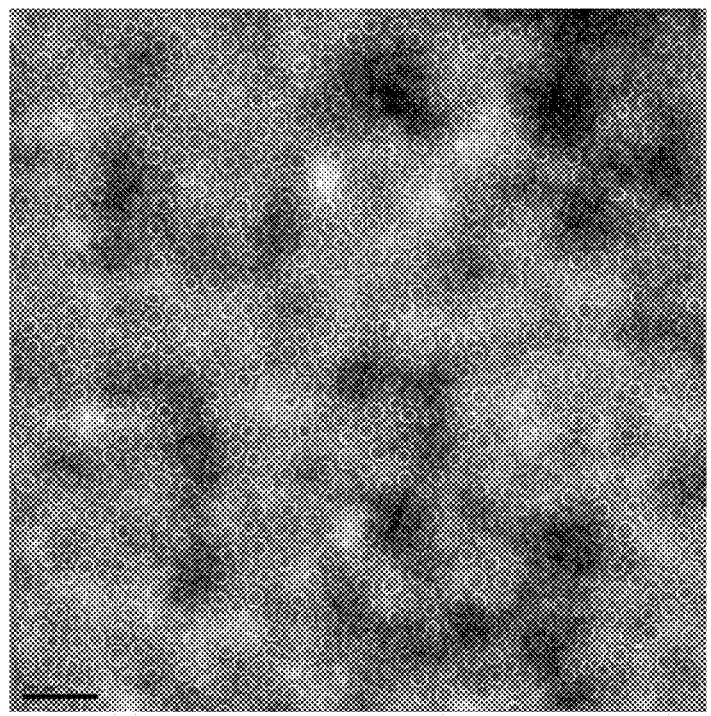
Figure 7E:
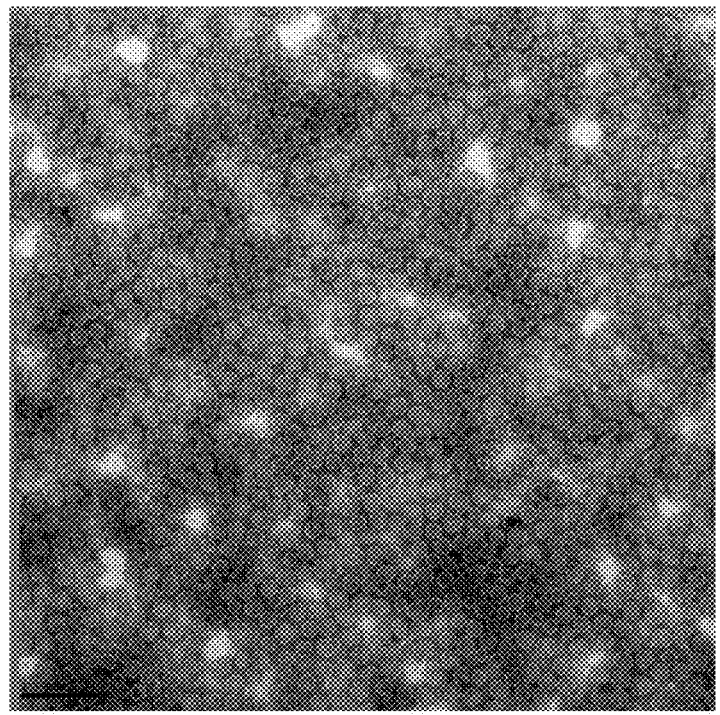
Figure 7F:
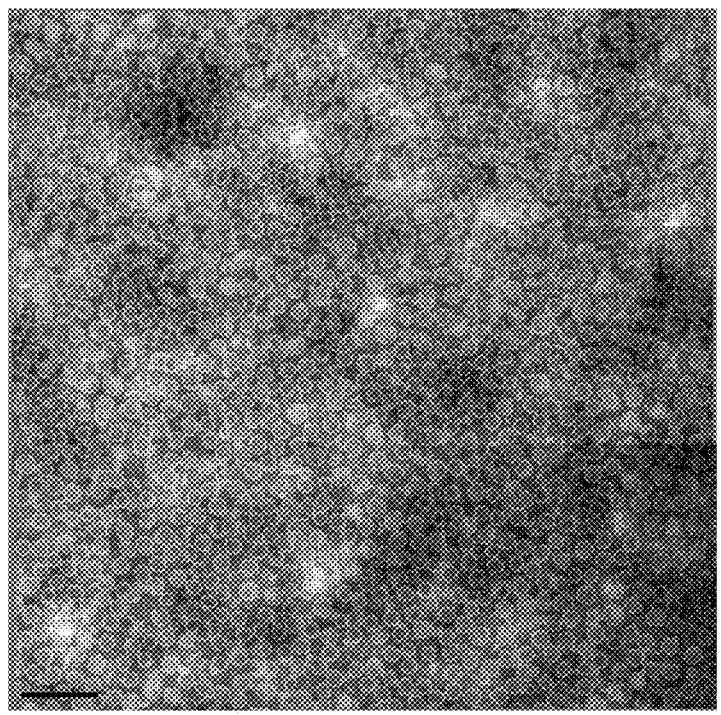
Figure 8A:
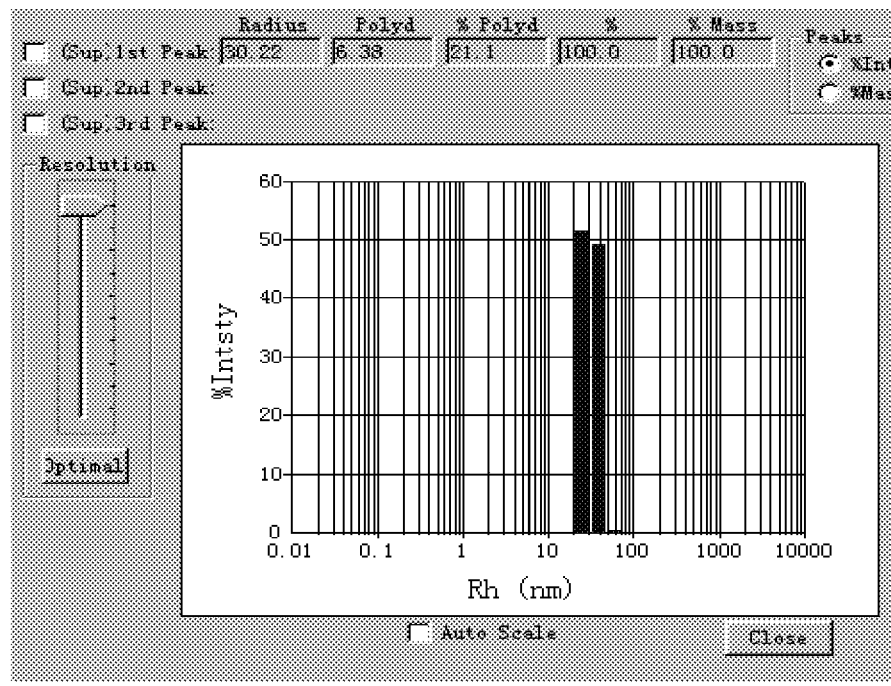
Figure 8B:
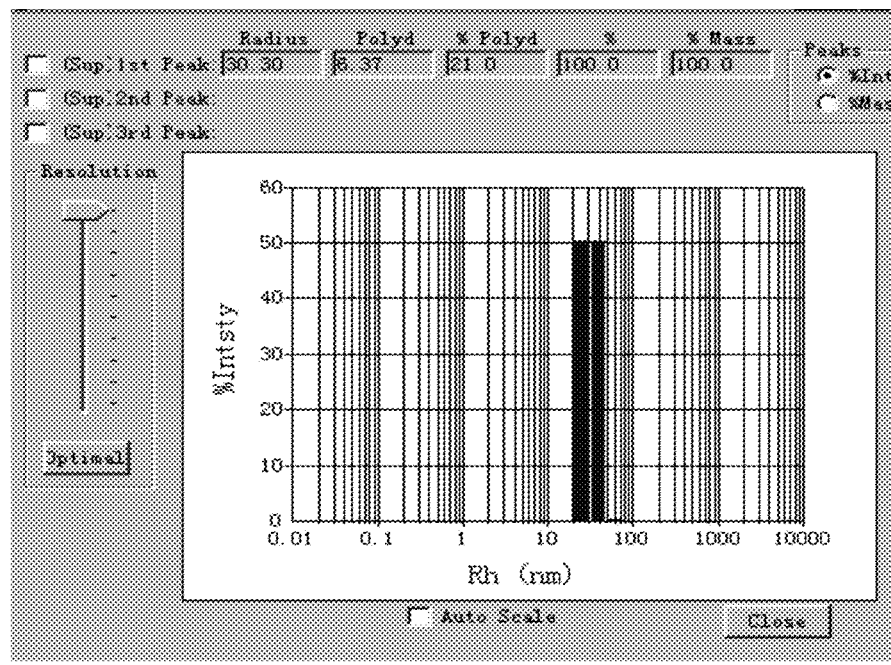
Figure 8C:
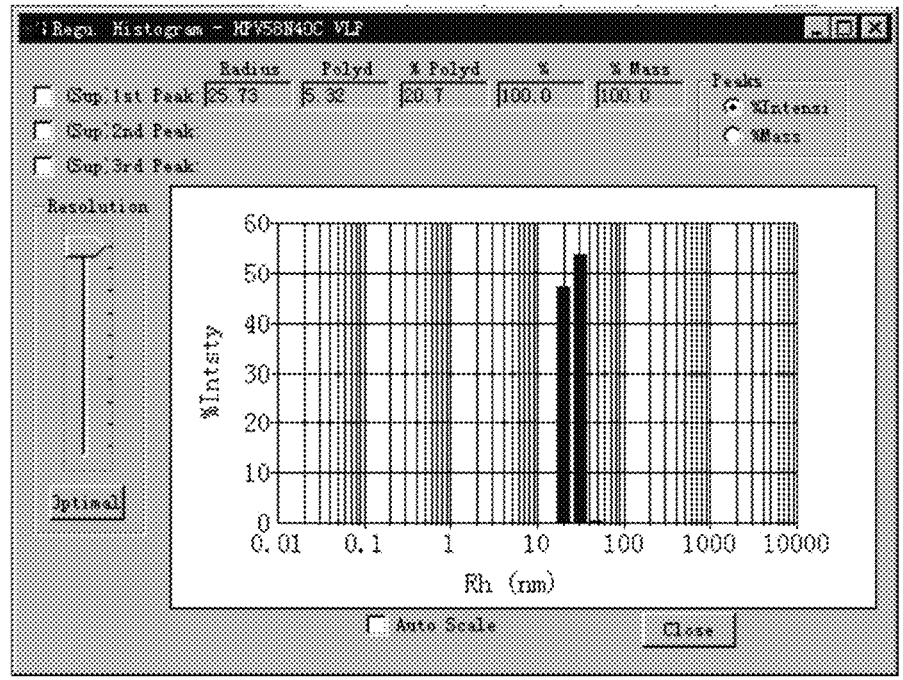
Figure 8D:
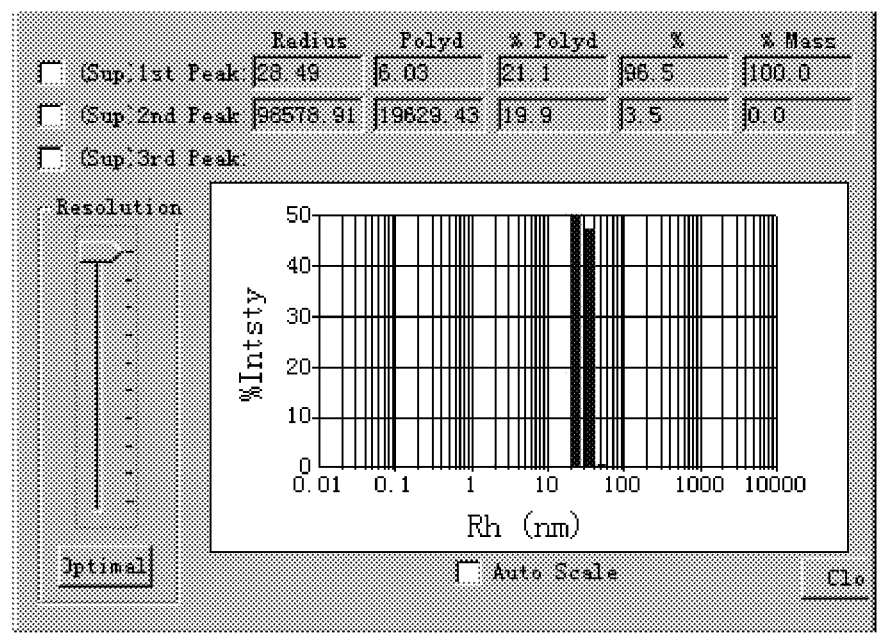
Figure 8E:
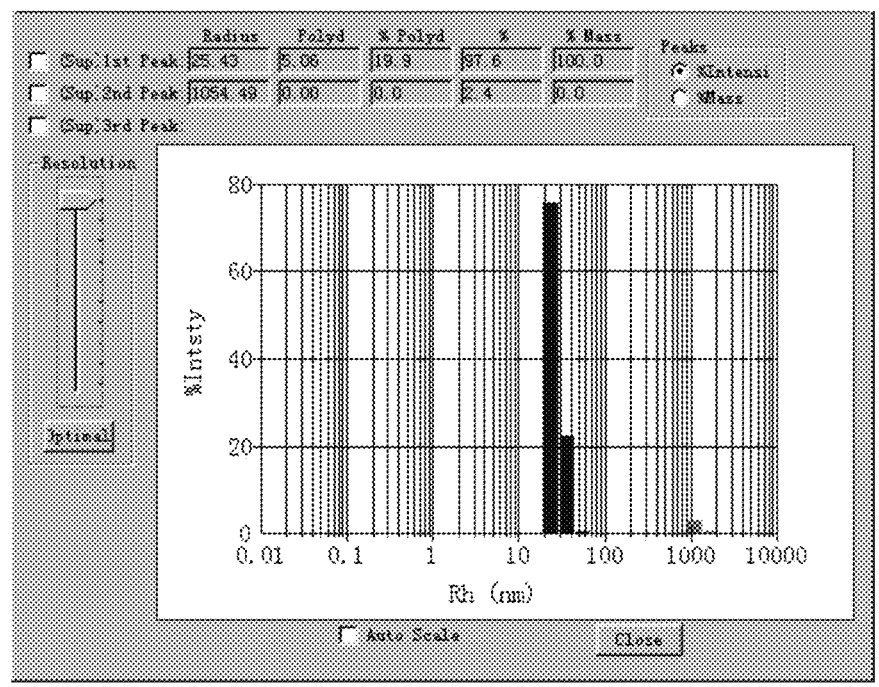
Figure 8F:
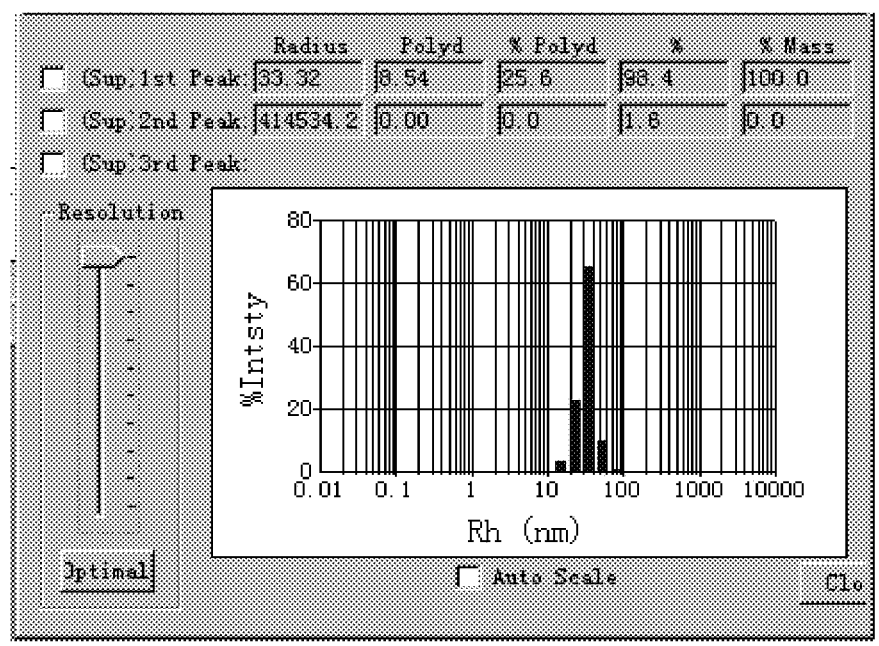

FIG. 6 shows the SDS-PAGE results of the HPV58 L1 proteins having 5, 15, 27, 40, 60 or 70 amino acids truncated at the N-terminal, respectively, i.e. HPV58N5C-L1, HPV58N15C-L1, HPV58N27C-L1, HPV58N40C-L1, HPV58N60C-L1, HPV58N70C-L1 (their amino acid sequences were set forth in SEQ ID NOs: 2, 3, 4, 5, 6 and 7, respectively), as obtained in Example 6. Lane M: protein molecular weight marker; Lane 1: the truncated HPV58 L1 protein HPV58N5C-L1 (the loading volume was 10 μL); Lane 2: the truncated HPV58 L1 protein HPV58N15C-L1 (the loading volume was 10 μL); Lane 3: the truncated HPV58 L1 protein HPV58N27C-L1 (the loading volume was 10 μL); Lane 4: the truncated HPV58 L1 protein HPV58N40C-L1 (the loading volume was 10 μL); Lane 5: the truncated HPV58 L1 protein HPV58N60C-L1 (the loading volume was 10 μL); Lane 6: the truncated HPV58 L1 protein HPV58N70C-L1 (the loading volume was 10 μL). The results show that the HPV58 L1 proteins having 5, 15, 27, 40, 60 or 70 amino acids truncated at the N-terminal, respectively, i.e. HPV58N5C-L1, HPV58N15C-L1, HPV58N27C-L1, HPV58N40C-L1, HPV58N60C-L1, HPV58N70C-L1, as obtained in Example 6, reached a purity above 98%.

FIG. 7 shows the transmission electron microscopy (TEM) photographs of HPV58N5C-L1, HPV58N15C-L1, HPV58N27C-L1, HPV58N40C-L1, HPV58N60C-L1, and HPV58N70C-L1 VLPs obtained in Example 6 (taken at 50,000× magnification, Bar=0.2 μm). FIG. 7A, HPV58N5C-L1 VLPs; FIG. 7B, HPV58N15C-L1 VLPs; FIG. 7C, HPV58N27C-L1 VLPs; FIG. 7D, HPV58N40C-L1 VLPs; FIG. 7E, HPV58N60C-L1 VLPs; FIG. 7F, HPV58N70C-L1 VLPs. The results showed that a large number of VLPs with a radius of about 25 nm were observed in visual field in FIGS. 7A-7F, wherein the particle size was consistent with the theoretic size and the particles were homogenous.

FIG. 8 shows the dynamic light-scattering measurement results of HPV58N5C-L1, HPV58N15C-L1, HPV58N27C-L1, HPV58N40C-L1, HPV58N60C-L1, and HPV58N70C-L1 VLPs obtained in Example 6. FIG. 8A, HPV58N5C-L1 VLPs; FIG. 8B, HPV58N15C-L1 VLPs; FIG. 8C, HPV58N27C-L1 VLPs; FIG. 8D, HPV58N40C-L1 VLPs; FIG. 8E, HPV58N60C-L1 VLPs; FIG. 8F, HPV58N70C-L1 VLPs. The results showed that HPV58N5C-L1, HPV58N15C-L1, HPV58N27C-L1, HPV58N40C-L1, HPV58N60C-L1, and HPV58N70C-L1 VLPs had a hydrodynamic radius of about 25 nm and a particle assembly rate of 100%.

SEQUENCE INFORMATION

The information on the sequences involved in the invention is provided in the following Table 1.

TABLE 1

| | Depiction of sequences |
|---|---|
| SEQ ID NO: | depiction |
| 1 | a HPV58 L1 protein having 35 amino acids truncated at its N-terminal, HPV58N35C-L1 |
| 2 | a HPV58 L1 protein having 5 amino acids truncated at its N-terminal, HPV58N5C-L1 |
| 3 | a HPV58 L1 protein having 15 amino acids truncated at its N-terminal, HPV58N15C-L1 |
| 4 | a HPV58 L1 protein having 27 amino acids truncated at its N-terminal, HPV58N27C-L1 |
| 5 | a HPV58 L1 protein having 40 amino acids truncated at its N-terminal, HPV58N40C-L1 |
| 6 | a HPV58 L1 protein having 60 amino acids truncated at its N-terminal, HPV58N60C-L1 |
| 7 | a HPV58 L1 protein having 70 amino acids truncated at its N-terminal, HPV58N70C-L1 |
| 8 | HPV58 L1 gene sequence (1575 bp) |
| 9 | a DNA sequence encoding SEQ ID NO: 1 |
| 10 | a DNA sequence encoding SEQ ID NO: 2 |
| 11 | a DNA sequence encoding SEQ ID NO: 3 |

TABLE 1 -continued

| 12 | a DNA sequence encoding SEQ ID NO: 4 |
| 13 | a DNA sequence encoding SEQ ID NO: 5 |
| 14 | a DNA sequence encoding SEQ ID NO: 6 |
| 15 | a DNA sequence encoding SEQ ID NO: 7 |
| 16 | primer |
| 17 | primer |

Sequence 1 (SEQ ID NO: 1):
MTVYLPPVPVSKVVSTDEYVSRTSIYYYAGSSRLLAVGNPYFSIKSPNNNKKVLVPKVSGLQYRVFRVRLPDPN
KFGFPDTSFYNPDTQRLYWACVGLEIGRGQPLGVGVSGHPYLNKFDDTETSNRYPAQPGSDNRECLSMDYKQTQ
LCLIGCKPPTGEHWGKGVACNNNAAATDCPPLELFNSIIEDGDMVDTGFGCMDFGTLQANKSDVPIDICNSTCK
YPDYLKMASEPYGDSLFFFLRREQMFVRHFFNRAGKLGEAVPDDLYIKGSGNTAVIQSSAFFPTPSGSIVTSES
QLFNKPYWLQRAQGHNNGICWGNQLFVTVVDTTRSTNMTLCTEVTKEGTYKNDNFKEYVRHVEEYDLQFVFQLC
KITLTAEIMTYIHTMDSNILEDWQFGLTPPPSASLQDTYRFVTSQAITCQKTAPPKEKEDPLNKYTFWEVNLKE
KFSADLDQFPLGRKFLLQSGLKAKPRLKRSAPTTRAPSTKRKKVKK Sequence 2 (SEQ ID NO: 2):
MCCTLAILFCVADVNVFHIFLQMSVWRPSEATVYLPPVPVSKVVSTDEYVSRTSIYYYAGSSRLLAVGNPYFSI
KSPNNNKKVLVPKVSGLQYRVFRVRLPDPNKFGFPDTSFYNPDTQRLVWACVGLEIGRGQPLGVGVSGHPYLNK
FDDTETSNRYPAQPGSDNRECLSMDYKQTQLCLIGCKPPTGEHWGKGVACNNNAAATDCPPLELFNSIIEDGDM
VDTGFGCMDFGTLQANKSDVPIDICNSTCKYPDYLKMASEPYGDSLFFFLRREQMFVRHFFNRAGKLGEAVPDD
LYIKGSGNTAVIQSSAFFPTPSGSIVTSESQLFNKPYWLQRAQGHNNGICWGNQLFVTVVDTTRSTNMTLCTEV
TKEGTYKNDNFKEYVRHVEEYDLQFVFQLCKITLTAEIMTYIHTMDSNILEDWQFGLTPPPSASLQDTYRFVTS
QAITCQKTAPPKEKEDPLNKYTFWEVNLKEKFSADLDQFPLGRKFLLQSGLKAKPRLKRSAPTTRAPSTKRKKV
KK Sequence 3 (SEQ ID NO: 3):
MADVNVFHIFLQMSVWRPSEATVYLPPVPVSKVVSTDEYVSRTSIYYYAGSSRLLAVGNPYFSIKSPNNNKVL
VPKVSGLQYRVFRVRLPDPNKFGFPDTSFYNPDTQRLVWACVGLEIGRGQPLGVGVSGHPYLNKFDDTETSNRY
PAQPGSDNRECLSMDYKQTQLCLIGCKPPTGEHWGKGVACNNNAAATDCPPLELFNSIIEDGDMVDTGFGCMDF
GTLQANKSDVPIDICNSTCKYPDYLKMASEPYGDSLFFFLRREQMFVRHFFNRAGKLGEAVPDDLYIKGSGNTA
VIQSSAFFPTPSGSIVTSESQLFNKPYWLQRAQGHNNGICWGNQLFVTVVDTTRSTNMTLCTEVTKEGTYKNDN
FKEYVRHVEEYDLQFVFQLCKITLTAEIMTYIHTMDSNILEDWQFGLTPPPSASLQDTYRFVTSQAITCQKTAP
PKEKEDPLNKYTFWEVNLKEKFSADLDQFPLGRKFLLQSGLKAKPRLKRSAPTTRAPSTKRKKVKK Sequence 4 (SEQ ID NO: 4):
MSVWRPSEATVYLPPVPVSKVVSTDEYVSRTSIYYYAGSSRLLAVGNPYFSIKSPNNNKKVLVPKVSGLQYRVF
RVRLPDPNKFGFPDTSFYNPDTQRLVWACVGLEIGRGQPLGVGVSGHPYLNKFDDTETSNRYPAQPGSDNRECL
SMDYKQTQLCLIGCKPPTGEHWGKGVACNNNAAATDCPPLELFNSIIEDGDMVDTGFGCMDFGTLQANKSDVPI
DICNSTCKYPDYLKMASEPYGDSLFFFLRREQMFVRHFFNRAGKLGEAVPDDLYIKGSGNTAVIQSSAFFPTPS
GSIVTSESQLFNKPYWLQRAQGHNNGICWGNQLFVTVVDTTRSTNMTLCTEVTKEGTYKNDNFKEYVRHVEEYD
LQFVFQLCKITLTAEIMTYIHTMDSNILEDWQFGLTPPPSASLQDTYRFVTSQAITCQKTAPPKEKEDPLNKYT
FWEVNLKEKFSADLDQFPLGRKFLLQSGLKAKPRLKRSAPTTRAPSTKRKKVKK Sequence 5 (SEQ ID NO: 5):
MPVPVSKVVSTDEYVSRTSIYYYAGSSRLLAVGNPYFSIKSPNNNKKVLVPKVSGLQYRVFRVRLPDPNKFGFP
DTSFYNPDTQRLVWACVGLEIGRGQPLGVGVSGHPYLNKFDDTETSNRYPAQPGSDNRECLSMDYKQTQLCLIG
CKPPTGEHWGKGVACNNNAAATDCPPLELFNSIIEDGDMVDTGFGCMDFGTLQANKSDVPIDICNSTCKYPDYL
KMASEPYGDSLFFFLRREQMFVRHFFNRAGKLGEAVPDDLYIKGSGNTAVIQSSAFFPTPSGSIVTSESQLFNK
PYWLQRAQGHNNGICWGNQLFVTVVDTTRSTNMTLCTEVTKEGTYKNDNFKEYVRHVEEYDLQFVFQLCKITLT
AEIMTYIHTMDSNILEDWQFGLTPPPSASLQDTYRFVTSQAITCQKTAPPKEKEDPLNKYTFWEVNLKEKFSAD
LDQFPLGRKFLLQSGLKAKPRLKRSAPTTRAPSTKRKKVKK Sequence 6 (SEQ ID NO: 6):
MYYAGSSRLLAVGNPYFSIKSPNNNKKVLVPKVSGLQYRVFRVRLPDPNKFGFPDTSFYNPDTQRLVWACVGLE
IGRGQPLGVGVSGHPYLNKFDDTETSNRYPAQPGSDNRECLSMDYKQTQLCLIGCKPPTGEHWGKGVACNNNAA
ATDCPPLELFNSIIEDGDMVDTGFGCMDFGTLQANKSDVPIDICNSTCKYPDYLKMASEPYGDSLFFFLRREQM
FVRHFFNRAGKLGEAVPDDLYIKGSGNTAVIQSSAFFPTPSGSIVTSESQLFNKPYWLQRAQGHNNGICWGNQL
FVTVVDTTRSTNMTLCTEVTKEGTYKNDNFKEYVRHVEEYDLQFVFQLCKITLTAEIMTYIHTMDSNILEDWQF
GLTPPPSASLQDTYRFVTSQAITCQKTAPPKEKEDPLNKYTFWEVNLKEKFSADLDQFPLGRKFLLQSGLKAKP
RLKRSAPTTRAPSTKRKKVKK Sequence 7 (SEQ ID NO: 7):
MVGNPYFSIKSPNNNKKVLVPKVSGLQYRVFRVRLPDPNKFGFPDTSFYNPDTQRLVWACVGLEIGRGQPLGVG
VSGHPYLNKFDDTETSNRYPAQPGSDNRECLSMDYKQTQLCLIGCKPPTGEHWGKGVACNNNAAATDCPPLELF
NSIIEDGDMVDTGFGCMDFGTLQANKSDVPIDICNSTCKYPDYLKMASEPYGDSLFFFLRREQMFVRHFFNRAG
KLGEAVPDDLYIKGSGNTAVIQSSAFFPTPSGSIVTSESQLFNKPYWLQRAQGHNNGICWGNQLFVTVVDTTRS
TNMTLCTEVTKEGTYKNDNFKEYVRHVEEYDLQFVFQLCKITLTAEIMTYIHTMDSNILEDWQFGLTPPPSASL
QDTYRFVTSQAITCQKTAPPKEKEDPLNKYTFWEVNLKEKFSADLDQFPLGRKFLLQSGLKAKPRLKRSAPTTR
APSTKRKKVKK Sequence 8 (SEQ ID NO: 8):
ATGGTGCTGATCCTGTGCTGCACCCTGGCCATCCTGTTCTGCGTGGCCGACGTGAACGTGTTCCACATCTTCCT
GCAGATGAGCGTGTGGAGGCCCAGCGAGGCCACCGTGTACCTGCCCCCCGTGCCCGTGAGCAAGGTGGTGAGCA
CCGACGAGTACGTGAGCAGGACCAGCATCTACTACTACGCCGGCAGCAGCAGGCTGCTGGCCGTGGGCAACCCC TABLE 1 -continued

```
TACTTCAGCATCAAGAGCCCCAACAACAACAAGAAGGTGCTGGTGCCCAAGGTGAGCGGCCTGCAGTACAGGGT
GTTCAGGGTGAGGCTGCCCGACCCCAACAAGTTCGGCTTCCCCGACACCAGCTTCTACAACCCCGACACCCAGA
GGCTGGTGTGGGCCTGCGTGGGCCTGGAGATCGGCAGGGGCCAGCCCCTGGGCGTGGGCGTGAGCGGCCACCCC
TACCTGAACAAGTTCGACGACACCGAGACCAGCAACAGGTACCCCGCCCAGCCCGGCAGCGACAACAGGGAGTG
CCTGAGCATGGACTACAAGCAGACCCAGCTGTGCCTGATCGGCTGCAAGCCCCCCACCGGCGAGCACTGGGGCA
AGGGCGTGGCCTGCAACAACAACGCCGCCGCCACCGACTGCCCCCCCCTGGAGCTGTTCAACAGCATCATCGAG
GACGGCGACATGGTGGACACCGGCTTCGGCTGCATGGACTTCGGCACCCTGCAGGCCAACAAGAGCGACGTGCC
CATCGACATCTGCAACAGCACCTGCAAGTACCCCGACTACCTGAAGATGGCCAGCGAGCCCTACGGCGACAGCC
TGTTCTTCTTCCTGAGGAGGGAGCAGATGTTCGTGAGGCACTTCTTCAACAGGGCCGGCAAGCTGGGCGAGGCC
GTGCCCGACGACCTGTACATCAAGGGCAGCGGCAACACCGCCGTGATCCAGAGCAGCGCCTTCTTCCCCACCCC
CAGCGGCAGCATCGTGACCAGCGAGAGCCAGCTGTTCAACAAGCCCTACTGGCTGCAGAGGGCCCAGGGCCACA
ACAACGGCATCTGCTGGGGCAACCAGCTGTTCGTGACCGTGGTGGACACCACCAGGAGCACCAACATGACCCTG
TGCACCGAGGTGACCAAGGAGGGCACCTACAAGAACGACAACTTCAAGGAGTACGTGAGGCACGTGGAGGAGTA
CGACCTGCAGTTCGTGTTCCAGCTGTGCAAGATCACCCTGACCGCCGAGATCATGACCTACATCCACACCATGG
ACAGCAACATCCTGGAGGACTGGCAGTTCGGCCTGACCCCCCCCCCCAGCGCCAGCCTGCAGGACACCTACAGG
TTCGTGACCAGCCAGGCCATCACCTGCCAGAAGACCGCCCCCCCCAAGGAGAAGGAGGACCCCCTGAACAAGTA
CACCTTCTGGGAGGTGAACCTGAAGGAGAAGTTCAGCGCCGACCTGGACCAGTTCCCCCTGGGCAGGAAGTTCC
TGCTGCAGAGCGGCCTGAAGGCCAAGCCCAGGCTGAAGAGGAGCGCCCCCACCACCAGGGCCCCCAGCACCAAG
AGGAAGAAGGTGAAGAAGTGA

Sequence 9 (SEQ ID NO: 9):
ATGACCGTGTACCTGCCCCCCGTGCCCGTGAGCAAGGTGGTGAGCACCGACGAGTACGTGAGCAGGACCAGCAT
CTACTACTACGCCGGCAGCAGCAGGCTGCTGGCCGTGGGCAACCCCTACTTCAGCATCAAGAGCCCCAACAACA
ACAAGAAGGTGCTGGTGCCCAAGGTGAGCGGCCTGCAGTACAGGGTGTTCAGGGTGAGGCTGCCCGACCCCAAC
AAGTTCGGCTTCCCCGACACCAGCTTCTACAACCCCGACACCCAGAGGCTGGTGTGGGCCTGCGTGGGCCTGGA
GATCGGCAGGGGCCAGCCCCTGGGCGTGGGCGTGAGCGGCCACCCCTACCTGAACAAGTTCGACGACACCGAGA
CCAGCAACAGGTACCCCGCCCAGCCCGGCAGCGACAACAGGGAGTGCCTGAGCATGGACTACAAGCAGACCCAG
CTGTGCCTGATCGGCTGCAAGCCCCCCACCGGCGAGCACTGGGGCAAGGGCGTGGCCTGCAACAACAACGCCGC
CGCCACCGACTGCCCCCCCCTGGAGCTGTTCAACAGCATCATCGAGGACGGCGACATGGTGGACACCGGCTTCG
GCTGCATGGACTTCGGCACCCTGCAGGCCAACAAGAGCGACGTGCCCATCGACATCTGCAACAGCACCTGCAAG
TACCCCGACTACCTGAAGATGGCCAGCGAGCCCTACGGCGACAGCCTGTTCTTCTTCCTGAGGAGGGAGCAGAT
GTTCGTGAGGCACTTCTTCAACAGGGCCGGCAAGCTGGGCGAGGCCGTGCCCGACGACCTGTACATCAAGGGCA
GCGGCAACACCGCCGTGATCCAGAGCAGCGCCTTCTTCCCCACCCCCAGCGGCAGCATCGTGACCAGCGAGAGC
CAGCTGTTCAACAAGCCCTACTGGCTGCAGAGGGCCCAGGGCCACAACAACGGCATCTGCTGGGGCAACCAGCT
GTTCGTGACCGTGGTGGACACCACCAGGAGCACCAACATGACCCTGTGCACCGAGGTGACCAAGGAGGGCACCT
ACAAGAACGACAACTTCAAGGAGTACGTGAGGCACGTGGAGGAGTACGACCTGCAGTTCGTGTTCCAGCTGTGC
AAGATCACCCTGACCGCCGAGATCATGACCTACATCCACACCATGGACAGCAACATCCTGGAGGACTGGCAGTT
CGGCCTGACCCCCCCCCCCAGCGCCAGCCTGCAGGACACCTACAGGTTCGTGACCAGCCAGGCCATCACCTGCC
AGAAGACCGCCCCCCCCAAGGAGAAGGAGGACCCCCTGAACAAGTACACCTTCTGGGAGGTGAACCTGAAGGAG
AAGTTCAGCGCCGACCTGGACCAGTTCCCCCTGGGCAGGAAGTTCCTGCTGCAGAGCGGCCTGAAGGCCAAGCC
CAGGCTGAAGAGGAGCGCCCCCACCACCAGGGCCCCCAGCACCAAGAGGAAGAAGGTGAAGAAGTAA Sequence 10 (SEQ ID NO: 10):
ATGTGCTGCACCCTGGCCATCCTGTTCTGCGTGGCCGACGTGAACGTGTTCCACATCTTCCTGCAGATGAGCGT
GTGGAGGCCCAGCGAGGCCACCGTGTACCTGCCCCCCGTGCCCGTGAGCAAGGTGGTGAGCACCGACGAGTACG
TGAGCAGGACCAGCATCTACTACTACGCCGGCAGCAGCAGGCTGCTGGCCGTGGGCAACCCCTACTTCAGCATC
AAGAGCCCCAACAACAACAAGAAGGTGCTGGTGCCCAAGGTGAGCGGCCTGCAGTACAGGGTGTTCAGGGTGAG
GCTGCCCGACCCCAACAAGTTCGGCTTCCCCGACACCAGCTTCTACAACCCCGACACCCAGAGGCTGGTGTGGG
CCTGCGTGGGCCTGGAGATCGGCAGGGGCCAGCCCCTGGGCGTGGGCGTGAGCGGCCACCCCTACCTGAACAAG
TTCGACGACACCGAGACCAGCAACAGGTACCCCGCCCAGCCCGGCAGCGACAACAGGGAGTGCCTGAGCATGGA
CTACAAGCAGACCCAGCTGTGCCTGATCGGCTGCAAGCCCCCCACCGGCGAGCACTGGGGCAAGGGCGTGGCCT
GCAACAACAACGCCGCCGCCACCGACTGCCCCCCCCTGGAGCTGTTCAACAGCATCATCGAGGACGGCGACATG
GTGGACACCGGCTTCGGCTGCATGGACTTCGGCACCCTGCAGGCCAACAAGAGCGACGTGCCCATCGACATCTG
CAACAGCACCTGCAAGTACCCCGACTACCTGAAGATGGCCAGCGAGCCCTACGGCGACAGCCTGTTCTTCTTCC
TGAGGAGGGAGCAGATGTTCGTGAGGCACTTCTTCAACAGGGCCGGCAAGCTGGGCGAGGCCGTGCCCGACGAC
CTGTACATCAAGGGCAGCGGCAACACCGCCGTGATCCAGAGCAGCGCCTTCTTCCCCACCCCCAGCGGCAGCAT
CGTGACCAGCGAGAGCCAGCTGTTCAACAAGCCCTACTGGCTGCAGAGGGCCCAGGGCCACAACAACGGCATCT
GCTGGGGCAACCAGCTGTTCGTGACCGTGGTGGACACCACCAGGAGCACCAACATGACCCTGTGCACCGAGGTG
ACCAAGGAGGGCACCTACAAGAACGACAACTTCAAGGAGTACGTGAGGCACGTGGAGGAGTACGACCTGCAGTT
CGTGTTCCAGCTGTGCAAGATCACCCTGACCGCCGAGATCATGACCTACATCCACACCATGGACAGCAACATCC
TGGAGGACTGGCAGTTCGGCCTGACCCCCCCCCCCAGCGCCAGCCTGCAGGACACCTACAGGTTCGTGACCAGC
CAGGCCATCACCTGCCAGAAGACCGCCCCCCCCAAGGAGAAGGAGGACCCCCTGAACAAGTACACCTTCTGGGA
GGTGAACCTGAAGGAGAAGTTCAGCGCCGACCTGGACCAGTTCCCCCTGGGCAGGAAGTTCCTGCTGCAGAGCG
GCCTGAAGGCCAAGCCCAGGCTGAAGAGGAGCGCCCCCACCACCAGGGCCCCCAGCACCAAGAGGAAGAAGGTG
AAGAAGTGA Sequence 11 (SEQ ID NO: 11):
ATGGCCGACGTGAACGTGTTCCACATCTTCCTGCAGATGAGCGTGTGGAGGCCCAGCGAGGCCACCGTGTACCT
GCCCCCCGTGCCCGTGAGCAAGGTGGTGAGCACCGACGAGTACGTGAGCAGGACCAGCATCTACTACTACGCCG
GCAGCAGCAGGCTGCTGGCCGTGGGCAACCCCTACTTCAGCATCAAGAGCCCCAACAACAACAAGAAGGTGCTG
GTGCCCAAGGTGAGCGGCCTGCAGTACAGGGTGTTCAGGGTGAGGCTGCCCGACCCCAACAAGTTCGGCTTCCC
CGACACCAGCTTCTACAACCCCGACACCCAGAGGCTGGTGTGGGCCTGCGTGGGCCTGGAGATCGGCAGGGGCC
AGCCCCTGGGCGTGGGCGTGAGCGGCCACCCCTACCTGAACAAGTTCGACGACACCGAGACCAGCAACAGGTAC
CCCGCCCAGCCCGGCAGCGACAACAGGGAGTGCCTGAGCATGGACTACAAGCAGACCCAGCTGTGCCTGATCGG
CTGCAAGCCCCCCACCGGCGAGCACTGGGGCAAGGGCGTGGCCTGCAACAACAACGCCGCCGCCACCGACTGCC
CCCCCCTGGAGCTGTTCAACAGCATCATCGAGGACGGCGACATGGTGGACACCGGCTTCGGCTGCATGGACTTC
GGCACCCTGCAGGCCAACAAGAGCGACGTGCCCATCGACATCTGCAACAGCACCTGCAAGTACCCCGACTACCT
GAAGATGGCCAGCGAGCCCTACGGCGACAGCCTGTTCTTCTTCCTGAGGAGGGAGCAGATGTTCGTGAGGCACT
TCTTCAACAGGGCCGGCAAGCTGGGCGAGGCCGTGCCCGACGACCTGTACATCAAGGGCAGCGGCAACACCGCC
GTGATCCAGAGCAGCGCCTTCTTCCCCACCCCCAGCGGCAGCATCGTGACCAGCGAGAGCCAGCTGTTCAACAA
```

TABLE 1 -continued

```
GCCCTACTGGCTGCAGAGGGCCCAGGGCCACAACAACGGCATCTGCTGGGGCAACCAGCTGTTCGTGACCGTGG
TGGACACCACCAGGAGCACCAACATGACCCTGTGCACCGAGGTGACCAAGGAGGGCACCTACAAGAACGACAAC
TTCAAGGAGTACGTGAGGCACGTGGAGGAGTACGACCTGCAGTTCGTGTTCCAGCTGTGCAAGATCACCCTGAC
CGCCGAGATCATGACCTACATCCACACCATGGACAGCAACATCCTGGAGGACTGGCAGTTCGGCCTGACCCCCC
CCCCAGCGCCAGCCTGCAGGACACCTACAGGTTCGTGACCAGCCAGGCCATCACCTGCCAGAAGACCGCCCCC
CCCAAGGAGAAGGAGGACCCCCTGAACAAGTACACCTTCTGGGAGGTGAACCTGAAGGAGAAGTTCAGCGCCGA
CCTGGACCAGTTCCCCCTGGGCAGGAAGTTCCTGCTGCAGAGCGGCCTGAAGGCCAAGCCCAGGCTGAAGAGGA
GCGCCCCCACCACCAGGGCCCCCAGCACCAAGAGGAAGAAGGTGAAGAAGTGA

Sequence 12 (SEQ ID NO: 12):
ATGAGCGTGTGGAGGCCCAGCGAGGCCACCGTGTACCTGCCCCCCGTGCCCGTGAGCAAGGTGGTGAGCACCGA
CGAGTACGTGAGCAGGACCAGCATCTACTACTACGCCGGCAGCAGCAGGCTGCTGGCCGTGGGCAACCCCTACT
TCAGCATCAAGAGCCCCAACAACAACAAGAAGGTGCTGGTGCCCAAGGTGAGCGGCCTGCAGTACAGGGTGTTC
AGGGTGAGGCTGCCCGACCCCAACAAGTTCGGCTTCCCCGACACCAGCTTCTACAACCCCGACACCCAGAGGCT
GGTGTGGGCCTGCGTGGGCCTGGAGATCGGCAGGGGCCAGCCCCTGGGCGTGGGCGTGAGCGGCCACCCCTACC
TGAACAAGTTCGACGACACCGAGACCAGCAACAGGTACCCCGCCCAGCCCGGCAGCGACAACAGGGAGTGCCTG
AGCATGGACTACAAGCAGACCCAGCTGTGCCTGATCGGCTGCAAGCCCCCCACCGGCGAGCACTGGGGCAAGGG
CGTGGCCTGCAACAACAACGCCGCCGCCACCGACTGCCCCCCCCTGGAGCTGTTCAACAGCATCATCGAGGACG
GCGACATGGTGGACACCGGCTTCGGCTGCATGGACTTCGGCACCCTGCAGGCCAACAAGAGCGACGTGCCCATC
GACATCTGCAACAGCACCTGCAAGTACCCCGACTACCTGAAGATGGCCAGCGAGCCCTACGCGACAGCCTGTT
CTTCTTCCTGAGGAGGGAGCAGATGTTCGTGAGGCACTTCTTCAACAGGGCCGGCAAGCTGGGCGAGGCCGTGC
CCGACGACCTGTACATCAAGGGCAGCGGCAACACCGCCGTGATCCAGAGCAGCGCCTTCTTCCCCACCCCCAGC
GGCAGCATCGTGACCAGCGAGAGCCAGCTGTTCAACAAGCCCTACTGGCTGCAGAGGGCCCAGGGCCACAACAA
CGGCATCTGCTGGGGCAACCAGCTGTTCGTGACCGTGGTGGACACCACCAGGAGCACCAACATGACCCTGTGCA
CCGAGGTGACCAAGGAGGGCACCTACAAGAACGACAACTTCAAGGAGTACGTGAGGCACGTGGAGGAGTACGAC
CTGCAGTTCGTGTTCCAGCTGTGCAAGATCACCCTGACCGCCGAGATCATGACCTACATCCACACCATGGACAG
CAACATCCTGGAGGACTGGCAGTTCGGCCTGACCCCCCCCCCAGCGCCAGCCTGCAGGACACCTACAGGTTCG
TGACCAGCCAGGCCATCACCTGCCAGAAGACCGCCCCCCCCAAGGAGAAGGAGGACCCCCTGAACAAGTACACC
TTCTGGGAGGTGAACCTGAAGGAGAAGTTCAGCGCCGACCTGGACCAGTTCCCCCTGGGCAGGAAGTTCCTGCT
GCAGAGCGGCCTGAAGGCCAAGCCCAGGCTGAAGAGGAGCGCCCCCACCACCAGGGCCCCCAGCACCAAGAGGA
AGAAGGTGAAGAAGTGA Sequence 13 (SEQ ID NO: 13):
ATGCCCGTGCCCGTGAGCAAGGTGGTGAGCACCGACGAGTACGTGAGCAGGACCAGCATCTACTACTACGCCGG
CAGCAGCAGGCTGCTGGCCGTGGGCAACCCCTACTTCAGCATCAAGAGCCCCAACAACAACAAGAAGGTGCTGG
TGCCCAAGGTGAGCGGCCTGCAGTACAGGGTGTTCAGGGTGAGGCTGCCCGACCCCAACAAGTTCGGCTTCCCC
GACACCAGCTTCTACAACCCCGACACCCAGAGGCTGGTGTGGGCCTGCGTGGGCCTGGAGATCGGCAGGGGCCA
GCCCCTGGGCGTGGGCGTGAGCGGCCACCCCTACCTGAACAAGTTCGACGACACCGAGACCAGCAACAGGTACC
CCGCCCAGCCCGGCAGCGACAACAGGGAGTGCCTGAGCATGGACTACAAGCAGACCCAGCTGTGCCTGATCGGC
TGCAAGCCCCCCACCGGCGAGCACTGGGGCAAGGGCGTGGCCTGCAACAACAACGCCGCCGCCACCGACTGCCC
CCCCCTGGAGCTGTTCAACAGCATCATCGAGGACGGCGACATGGTGGACACCGGCTTCGGCTGCATGGACTTCG
GCACCCTGCAGGCCAACAAGAGCGACGTGCCCATCGACATCTGCAACAGCACCTGCAAGTACCCCGACTACCTG
AAGATGGCCAGCGAGCCCTACGGCGACAGCCTGTTCTTCTTCCTGAGGAGGGAGCAGATGTTCGTGAGGCACTT
CTTCAACAGGGCCGGCAAGCTGGGCGAGGCCGTGCCCGACGACCTGTACATCAAGGGCAGCGGCAACACCGCCG
TGATCCAGAGCAGCGCCTTCTTCCCCACCCCCAGCGGCAGCATCGTGACCAGCGAGAGCCAGCTGTTCAACAAG
CCCTACTGGCTGCAGAGGGCCCAGGGCCACAACAACGGCATCTGCTGGGGCAACCAGCTGTTCGTGACCGTGGT
GGACACCACCAGGAGCACCAACATGACCCTGTGCACCGAGGTGACCAAGGAGGGCACCTACAAGAACGACAACT
TCAAGGAGTACGTGAGGCACGTGGAGGAGTACGACCTGCAGTTCGTGTTCCAGCTGTGCAAGATCACCCTGACC
GCCGAGATCATGACCTACATCCACACCATGGACAGCAACATCCTGGAGGACTGGCAGTTCGGCCTGACCCCCCC
CCCCAGCGCCAGCCTGCAGGACACCTACAGGTTCGTGACCAGCCAGGCCATCACCTGCCAGAAGACCGCCCCCC
CCAAGGAGAAGGAGGACCCCCTGAACAAGTACACCTTCTGGGAGGTGAACCTGAAGGAGAAGTTCAGCGCCGAC
CTGGACCAGTTCCCCCTGGGCAGGAAGTTCCTGCTGCAGAGCGGCCTGAAGGCCAAGCCCAGGCTGAAGAGGAG
CGCCCCCACCACCAGGGCCCCCAGCACCAAGAGGAAGAAGGTGAAGAAGTAA Sequence 14 (SEQ ID NO: 14):
ATGTACTACGCCGGCAGCAGCAGGCTGCTGGCCGTGGGCAACCCCTACTTCAGCATCAAGAGCCCCAACAACAA
CAAGAAGGTGCTGGTGCCCAAGGTGAGCGGCCTGCAGTACAGGGTGTTCAGGGTGAGGCTGCCCGACCCCAACA
AGTTCGGCTTCCCCGACACCAGCTTCTACAACCCCGACACCCAGAGGCTGGTGTGGGCCTGCGTGGGCCTGGAG
ATCGGCAGGGGCCAGCCCCTGGGCGTGGGCGTGAGCGGCCACCCCTACCTGAACAAGTTCGACGACACCGAGAC
CAGCAACAGGTACCCCGCCCAGCCCGGCAGCGACAACAGGGAGTGCCTGAGCATGGACTACAAGCAGACCCAGC
TGTGCCTGATCGGCTGCAAGCCCCCCACCGGCGAGCACTGGGGCAAGGGCGTGGCCTGCAACAACAACGCCGCC
GCCACCGACTGCCCCCCCCTGGAGCTGTTCAACAGCATCATCGAGGACGGCGACATGGTGGACACCGGCTTCGG
CTGCATGGACTTCGGCACCCTGCAGGCCAACAAGAGCGACGTGCCCATCGACATCTGCAACAGCACCTGCAAGT
ACCCCGACTACCTGAAGATGGCCAGCGAGCCCTACGGCGACAGCCTGTTCTTCTTCCTGAGGAGGGAGCAGATG
TTCGTGAGGCACTTCTTCAACAGGGCCGGCAAGCTGGGCGAGGCCGTGCCCGACGACCTGTACATCAAGGGCAG
CGGCAACACCGCCGTGATCCAGAGCAGCGCCTTCTTCCCCACCCCCAGCGGCAGCATCGTGACCAGCGAGAGCC
AGCTGTTCAACAAGCCCTACTGGCTGCAGAGGGCCCAGGGCCACAACAACGGCATCTGCTGGGGCAACCAGCTG
TTCGTGACCGTGGTGGACACCACCAGGAGCACCAACATGACCCTGTGCACCGAGGTGACCAAGGAGGGCACCTA
CAAGAACGACAACTTCAAGGAGTACGTGAGGCACGTGGAGGAGTACGACCTGCAGTTCGTGTTCCAGCTGTGCA
AGATCACCCTGACCGCCGAGATCATGACCTACATCCACACCATGGACAGCAACATCCTGGAGGACTGGCAGTTC
GGCCTGACCCCCCCCCCCAGCGCCAGCCTGCAGGACACCTACAGGTTCGTGACCAGCCAGGCCATCACCTGCCA
GAAGACCGCCCCCCCCAAGGAGAAGGAGGACCCCCTGAACAAGTACACCTTCTGGGAGGTGAACCTGAAGGAGA
AGTTCAGCGCCGACCTGGACCAGTTCCCCCTGGGCAGGAAGTTCCTGCTGCAGAGCGGCCTGAAGGCCAAGCCC
AGGCTGAAGAGGAGCGCCCCCACCACCAGGGCCCCCAGCACCAAGAGGAAGAAGGTGAAGAAGTGA Sequence 15 (SEQ ID NO: 15):
ATGGTGGGCAACCCCTACTTCAGCATCAAGAGCCCCAACAACAACAAGAAGGTGCTGGTGCCCAAGGTGAGCGG
CCTGCAGTACAGGGTGTTCAGGGTGAGGCTGCCCGACCCCAACAAGTTCGGCTTCCCCGACACCAGCTTCTACA
ACCCCGACACCCAGAGGCTGGTGTGGGCCTGCGTGGGCCTGGAGATCGGCAGGGGCCAGCCCCTGGGCGTGGGC
GTGAGCGGCCACCCCTACCTGAACAAGTTCGACGACACCGAGACCAGCAACAGGTACCCCGCCCAGCCCGGCAG
```

TABLE 1 -continued

```
CGACAACAGGGAGTGCCTGAGCATGGACTACAAGCAGACCCAGCTGTGCCTGATCGGCTGCAAGCCCCCACCG
GCGAGCACTGGGGCAAGGGCGTGGCCTGCAACAACAACGCCGCCGCCACCGACTGCCCCCCCCTGGAGCTGTTC
AACAGCATCATCGAGGACGGCGACATGGTGGACACCGGCTTCGGCTGCATGGACTTCGGCACCCTGCAGGCCAA
CAAGAGCGACGTGCCCATCGACATCTGCAACAGCACCTGCAAGTACCCCGACTACCTGAAGATGGCCAGCGAGC
CCTACGGCGACAGCCTGTTCTTCTTCCTGAGGAGGGAGCAGATGTTCGTGAGGCACTTCTTCAACAGGGCCGGC
AAGCTGGGCGAGGCCGTGCCCGACGACCTGTACATCAAGGGCAGCGGCAACACCGCCGTGATCCAGAGCAGCGC
CTTCTTCCCCACCCCCAGCGGCAGCATCGTGACCAGCGAGAGCCAGCTGTTCAACAAGCCCTACTGGCTGCAGA
GGGCCCAGGGCCACAACAACGGCATCTGCTGGGGCAACCAGCTGTTCGTGACCGTGGTGGACACCACCAGGAGC
ACCAACATGACCCTGTGCACCGAGGTGACCAAGGAGGGCACCTACAAGAACGACAACTTCAAGGAGTACGTGAG
GCACGTGGAGGAGTACGACCTGCAGTTCGTGTTCCAGCTGTGCAAGATCACCCTGACCGCCGAGATCATGACCT
ACATCCACACCATGGACAGCAACATCCTGGAGGACTGGCAGTTCGGCCTGACCCCCCCCCCAGCGCCAGCCTG
CAGGACACCTACAGGTTCGTGACCAGCCAGGCCATCACCTGCCAGAAGACCGCCCCCCCCAAGGAGAAGGAGGA
CCCCCTGAACAAGTACACCTTCTGGGAGGTGAACCTGAAGGAGAAGTTCAGCGCCGACCTGGACCAGTTCCCCC
TGGGCAGGAAGTTCCTGCTGCAGAGCGGCCTGAAGGCCAAGCCCAGGCTGAAGAGGAGCGCCCCCACCACCAGG
GCCCCCAGCACCAAGAGGAAGAAGGTGAAGAAGTGA

Sequence 16 (SEQ ID NO: 16):
CATATgAccgTgTAccTgccc

Sequence 17 (SEQ ID NO: 17):
gTCgACTTACTTCTTCACCTTCTTCC
```

Specific Modes for Carrying Out the Invention

The present invention is further illustrated in detail by reference to the examples as follows. It is understood by those skilled in the art that the examples are used only for the purpose of illustrating the present invention, rather than limiting the protection scope of the present invention.

Unless indicated otherwise, the molecular biological experimental methods and immunological assays used in the present invention are carried out substantially in accordance with the methods as described in Sambrook J et al., Molecular Cloning: A Laboratory Manual (Second Edition), Cold Spring Harbor Laboratory Press, 1989, and F. M. Ausubel et al., Short Protocols in Molecular Biology, 3$^{rd}$ Edition, John Wiley & Sons, Inc., 1995, or in accordance with the product instructions. The reagents and instruments used in the present invention without marking out their manufacturers are all conventional products commercially available from markets. Those skilled in the art understand that the examples are used for illustrating the present invention, but not intended to limit the protection scope of the present invention.

EXAMPLE 1

Expression of the Truncated HPV58 L1 Proteins with a Sequence as Set Forth in SEQ ID NO: 1

Preparation of Full-Length HPV58 L1 Gene as a Template

The full-length HPV58 L1 gene as a template was synthesized by Shanghai Boya Bio Co. The synthesized gene fragment has a full length of 1575 bp, and its sequence is as set forth in SEQ ID NO: 8. On the basis of the synthetic full-length HPV58 L1 gene fragment, the polynucleotides encoding the truncated HPV58 L1 proteins according to the invention were prepared.

Construction of Non-Fusion Expression Vectors for Expressing the Truncated HPV58 L1 Proteins The full-length HPV58 L1 gene as synthesized in the previous step was used as the template for the PCR reaction. The forward primer was 58N35F: 5'-cATATg Acc gTg TAc cTg ccc-3' (SEQ ID NO: 16), at the 5' terminal of which the restriction endonuclease NdeI site CAT ATG was introduced, wherein ATG was the initiation codon in E. coli system. The reverse primer was 58CR: 5'-gTCgAC TTA CTT CTT CAC CTT CTT CC-3' (SEQ ID NO: 17), at the 5' terminal of which the restriction endonuclease SalI site was introduced. The PCR reaction was performed in a PCR thermocycler (Biometra T3) under the following conditions:

| | |
|---|---|
| 94° C. denaturation for 10 min | 1 cycle |
| 94° C. denaturation for 50 sec | 15 cycles |
| 56° C. annealing for 50 sec | |
| 72° C. elongation for 1.5 min | |
| 72° C. elongation for 10 min | 1 cycle |

The DNA fragments, about 1.5 kb in length, were obtained after amplification. The PCR products were linked into the commercially available pMD 18-T vector (Takara Biosciences), and were then transformed into E. coli DH5α. Positive bacterial colonies were screened, and plasmids were extracted. After digestion with NdeI/SalI, it was identified that positive clones, designated as pMD 18-T-HPV58N35C-L1, were obtained, wherein the truncated HPV58 L1 gene was inserted.

The nucleotide sequence of the fragment of interest, which was inserted into the plasmid pMD 18-T-HPV58N35C-L1, was determined as SEQ ID NO: 9 by Shanghai Boya Bio Co. using M13 (+)/(−) primers, and the amino acid sequence encoded thereby was set forth in SEQ ID NO: 1. The sequence corresponded to a HPV58 L1 protein having 35 amino acids truncated at its N-terminal and no amino acid truncated at its C-terminal, designated as HPV58N35C-L1.

The HPV58N35C-L1 gene fragment was obtained by NdeI/SalI digestion of the plasmid pMD 18-T-HPV58N35C-L1. The fragment was linked to the non-fusion expression vector pTO-T7 (Luo wenxin et al. Chinese Journal of Biotechnology, 2000, 16: 53-57) digested with NdeI/SalI, and was then transformed into E. coli ER2566. Positive bacterial colonies were screened, and plasmids were extracted. After digestion with NdeI/SalI, it was identified that positive clones, designated as pTO-T7-HPV58N35C-L1, were obtained, wherein the fragment of interest was inserted.

1 μL of the plasmid pTO-T7-HPV58N35C-L1 (0.15 mg/ml) was taken to transform 40 μL competent E. coli ER2566 (purchased from New England Biolabs) prepared by Calcium chloride method, and then the bacteria were plated on solid LB medium (the components of the LB medium: 10 g/L peptone, 5 g/L yeast powder, and 10 g/L NaCl, the same as below) containing kanamycin (at a final concentration of 25 mg/ml, the same as below). Plates were statically incubated at 37° C. for about 10-12 h until single colonies could be observed clearly. Single colonies from the plates were transferred to a tube containing 4 ml liquid LB media containing kanamycin. Cultures were incubated in a shaking incubator at 220 rpm for 10 h at 37° C., and then 1 ml bacterial solution was taken and stored at −70° C.

Expression of HPV58N35C-L1 Protein on Large Scale

The *E. coli* solution carrying the recombinant plasmid pT0-T7-HPV58N35C-L1 at −70° C. as prepared in the previous step was seeded in 50 mL LB liquid medium containing kanamycin and incubated at 200 rpm and 37° C. for about 8 h. Then, the cultures were transferred to ten flasks (5 ml cultures per flask), each of which contained 500 mL LB medium containing kanamycin, and then were incubated in a shaking incubator overnight at 200 rpm and 37° C., as a starter culture.

A 50 L fermenter made by Shanghai Baoxing Biological Ltd was used in large-scale culture. PH electrode of the fermenter was calibrated. 30 L LB medium was loaded into the fermenter, in situ sterilized at 121° C. for 30 minutes. Oxygen-dissolved electrode was calibrated, wherein the value was determined as 0 prior to introduction of air after sterilization and as 100% prior to vaccination after introduction of air while stirring at an initial rate of 100 rpm.

Preparation of the feed: The mixture of peptone and yeast extract at a concentration of 30% is prepared (20 g peptone and 10 g yeast extract were dissolved in 100 mL); a glucose solution of 50% is prepared (50 g glucose was dissolved in 100 ml). The two solutions were sterilized at 121° C. for 20 min.

On the next day, the starter cultures in the ten flasks (for a total of 5 L) were transferred to the fermenter. A temperature of 37° C. and a pH value of 7.0 were set, the dissolved $O_2$ was maintained at >40% by regulating agitation rate and air supply manually.

Flow Feed: the glucose solution (50%) and the mixture of peptone and yeast extract (30%) were mixed at a solute mass ratio of 2:1.

Flow rates were as followed (25 ml/min was defined as 100%):

$1^{st}$ h: 5%
$2^{nd}$ h: 10%
$3^{rd}$ h: 20%
$4^{th}$ h: 40%
$5^{th}$ h to the end: 60%

When the bacterial concentration reached an $OD_{600}$ of about 10.0, the culturing temperature was lowered to 25° C. and 4 g IPTG was added to initiate an induction culture of 4 h. Fermentation was halted when the final concentration reached an $OD_{600}$ of about 60. The bacteria were collected by centrifugation. The bacteria expressing HPV58N35C-L1 protein were obtained, weighted about 2.5 kg.

EXAMPLE 2

Preparation of HPV58N35C-L1 Protein with a Purity of about 70%

Figure 1:
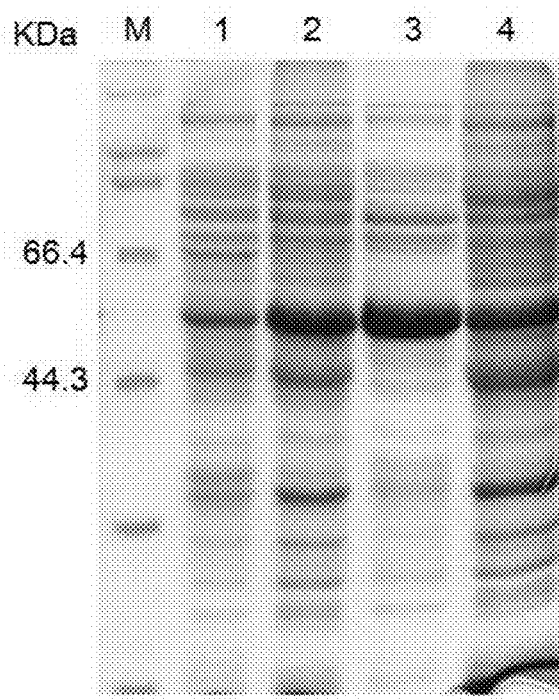
FIG. 1 shows the SDS-PAGE result of the HPV58N35C-L1 protein obtained during different steps of Example 2 of the invention. Lane M: protein molecular weight marker; Lane 1: supernatant of disrupted bacteria (i.e. the supernatant obtained by centrifuging the disrupted bacteria); Lane 2: precipitate product free of salts (i.e. the precipitate obtained by centrifugation after dialysis); Lane 3: re-dissolved supernatant (i.e. the supernatant obtained by centrifuging the solution resulted from re-dissolving the precipitate product free of salts); Lane 4: precipitant obtained after re-dissolution (i.e. the precipitate obtained by centrifuging the solution resulted from re-dissolving the precipitate product free of salts). The result showed that the purity of HPV58N35C-L1 protein was increased from about 10% (see Lane 1) to about 70% (see Lane 3) after the steps of precipitation and re-dissolution.

Bacteria were re-suspended at a proportion of 1 g bacteria corresponding to 10 ml lysis buffer (20 mM Tris buffer pH 7.2, 300 mM NaCl). Bacteria were disrupted by an APV homogenizer (Invensys Group) for five times at a pressure of 600 bar. The homogenate was centrifuged at 13,500 rpm (30,000 g) using JA-14 rotor for 15 min, and the supernatant (i.e. the supernatant of disrupted bacteria) was obtained. The supernatant was subjected to 10% SDS-PAGE. At this stage, the HPV58N35C-L1 protein in the supernatant had a purity of about 10% (see FIG. 1, Lane 1).

The supernatant was dialyzed by a CENTRASETTE 5 Tangential Flow Filter (Pall Co.) running at a pressure of 0.5 psi, a flow rate of 500 ml/min, and a tangential flow rate of 200 mL/min, wherein the membrane retention molecular weight was 30 kDa, the dialysis solution was 10 mM phosphate buffer pH 6.0, and the dialysis volume was three times of the volume of the supernatant.

After thorough dialysis, the mixture was centrifuged at 9500 rpm (12,000 g) using JA-10 rotor (Beckman J25 high speed centrifuge)) for 20 min, and the precipitate (i.e. the precipitate product free of salts) was collected. The precipitate was re-suspended in 20 mM phosphate buffer (pH 8.0) containing 20 mM DTT and 600 mM NaCl, wherein the volume of the buffer was 1/10 of the volume of the supernatant. The mixture was stirred for 30 min and centrifuged at 13,500 rpm (30,000 g) using JA-14 rotor (Beckman J25 high speed centrifuge) for 20 min. The supernatant and precipitate (i.e. the precipitate obtained after re-dissolution) were collected. The supernatant was diluted with 20 mM phosphate buffer (pH 8.0) containing 20 mM DTT of an equal volume, resulting in the final NaCl concentration of 0.3 M. Then, the diluted supernatant was filtered using a filter membrane with an aperture of 0.22 μm. The sample obtained (i.e. re-dissolved supernatant) was purified by cation exchange chromatography (as described in Example 3). 30 μL of 6× loading buffer (12% (w/v) SDS, 0.6% (w/v) bromophenol blue, 0.3M Tris-HCl pH 6.8, 60% (v/v) glycerin, 5% (v/v) (3-mercaptoethanol) was added to 150 μL filtered supernatant, and the result solution was mixed homogeneously and was placed in a water bath at 80° C. for 10 min. Then, 10 μl sample was subjected to 10% SDS-PAGE at 120V for 120 min. The electrophoretic bands were stained by Coomassie brilliant blue. The electrophoretic result was shown in FIG. 1. The result showed that HPV58N35C-L1 protein was purified and enriched after the steps of precipitation and re-dissolution, with its purity increased from about 10% to about 70% (see FIG. 1, Lane 1 and Lane 3).

EXAMPLE 3

Chromatographic Purification of HPV58N35C-L1 Protein

1) Purification of HPV58N35C-L1 Protein by Cation Exchange Chromatography

Equipment: AKTA Explorer 100 preparative liquid chromatography system produced by GE Healthcare (i.e. the original Amershan Pharmacia Co.)

Chromatographic media: SP Sepharose 4 Fast Flow (GE Healthcare Co.)

Column Volume: 5.5 cm×20 cm
Buffer: 20 mM phosphate buffer pH 8.0, 20 mM DTT
20 mM phosphate buffer pH 8.0, 20 mM DTT, 2M NaCl
Flow Rate: 25 mL/min
Detector Wavelength: 280 nm
Sample: about 70% pure HPV58N35C-L1 protein solution, as filtered through a filter membrane with an aperture of 0.22 μm in Example 2.

Elution protocol: eluting undesired proteins with 500 mM NaCl, eluting the protein of interest with 1000 mM NaCl, collecting eluate eluted with 1000 mM NaCl, and finally getting about 900 mL purified HPV58N35C-L1 sample.

2) Purification of HPV58N35C-L1 by CHT-II Chromatography (Hydroxyapatite Chromatography)

Equipment: AKTA Explorer 100 preparative liquid chromatography system produced by GE Healthcare (i.e. the original Amershan Pharmacia Co.)

Chromatographic media: CHT-II (purchased from Bio-Rad)
Column Volume: 5.5 cm×20 cm
Buffer: 20 mM phosphate buffer pH8.0, 20 mM DTT,
20 mM phosphate buffer pH 8.0, 20 mM DTT, 2M NaCl
Flow Rate: 20 mL/min
Detector Wavelength: 280 nm
Sample: 1000 mM NaCl elution product obtained in the previous step, diluted to a NaCl concentration of 0.3M with 20 mM phosphate buffer pH 8.0, 20 mM DTT.
Elution protocol: eluting undesired proteins with 500 mM NaCl, eluting the protein of interest with 1000 mM NaCl, collecting eluate eluted with 1000 mM NaCl, and finally getting 800 mL purified HPV58N35C-L1 sample.

Figure 2:
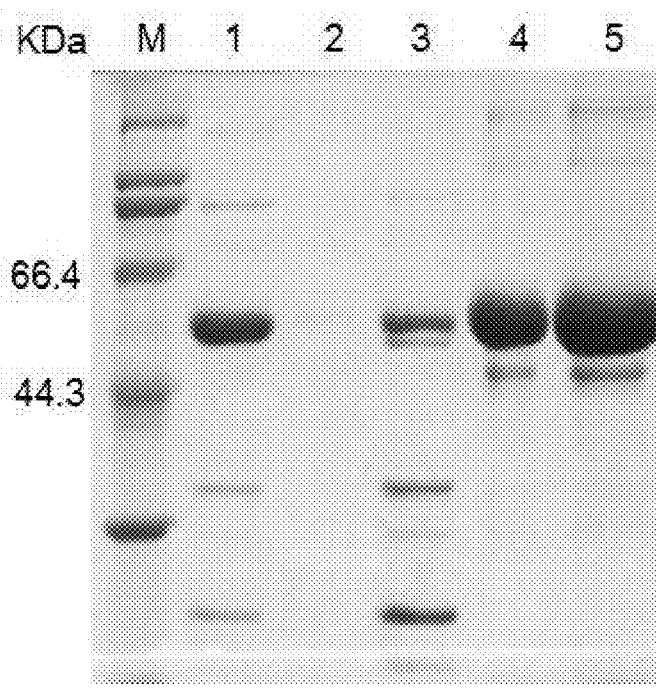
FIG. 2 shows the SDS-PAGE result of HPV58N35C-L1 purified by cation exchange chromatography and CHT-II (hydroxyapatite chromatography) in Example 3. Lane M: protein molecular weight marker; Lane 1: sample before purification with CHT-II column; Lane 2: flow-through fraction during purification with CHT-II column; Lane 3: elution fraction eluted with 500 mmol/L NaCl; Lane 4: elution fraction eluted with 1000 mmol/L NaCl (the loading volume was 10

30 µL 6× loading buffer was added to 150 µL HPV58N35C-L1 sample as purified by the method in the present Example, and then the result solution was mixed homogeneously. After incubating the solution in a water bath at 80° C. for 10 min, a 10 µL sample was subjected to 10% SDS-PAGE at 120V for 120 min. The electrophoretic bands were stained by Coomassie brilliant blue. The electrophoretic result was shown in FIG. 2. The result showed that after said purification step, the concentration of HPV58N35C-L1 protein was about 1.0 mg/ml, with a purity of greater than 98%.

EXAMPLE 4

Assembly of HPV58N35C-L1 VLPs

Equipment: CENTRASETTE 5 Tangential Flow Filter (Pall Co.), wherein the membrane retention molecular weight was 30 kDa. Sample: HPV58N35C-L1 with a purity of greater than 98% as obtained in Example 3.

Sample Renaturation: Sample buffer was exchanged with 10L renaturation buffer (50 mM PB (sodium phosphate buffer) pH 6.0, 2 mM $CaCl_2$, 2 mM $MgCl_2$, 0.5M NaCl, 0.003% TWEEN-80®) thoroughly. The Tangential Flow Filter was run at a pressure of 0.5 psi and a tangential flow rate of 10 mL/min. When the exchange with renaturation buffer was finished, the renaturation buffer was exchanged with storage buffer (20L PBS: 20mM PB pH 6.5, 0.5M NaCl) with an exchange volume of 20L. The Tangential Flow Filter was run at a pressure of 0.5 psi and a tangential flow rate of 25 mL/min. When the exchange was finished, the sample was aseptically filtrated with a Pall filter (0.20 µm), and thereby obtaining HPV58N35C-L1VLPs. The HPV58N35C-L1 VLPs were stored at 4° C. for further use.

EXAMPLE 5

Determination of the Morphology of HPV58N35C-L1 VLPs and Determination of Immunogenicity Thereof Transmission Electron Microscopy (TEM) of HPV58N35C-L1 VLPs The equipment was a JEOL 100 kV Transmission Electron Microscope (100,000× magnification). HPV58N35C-L1 VLPs obtained in Example 4 were negatively stained with 2% phosphotungstic acid at pH 7.0, and fixed on a copper grid for observation. Results were shown in FIG. 3. A large number of VLPs with a radius of approximately 25 nm, which were homogenous and in a hollow form, were observed.

Dynamic Light-Scattering Measurement of HPV58N35C-L1 VLPs

DynaPro MS/X dynamic light-scattering instrument (including a temperature controller) (US Protein Solutions Co.) was used for light-scattering measurements. The regulation algorithm was used in the measurements. The sample was the HPV58N35C-L1 VLPs obtained in Example 4. The sample was passed through a 0.22 µm filter membrane prior to the measurement. The result was shown in FIG. 4. The result showed that HPV58N35C-L1 VLPs had a Hydrodynamic radius of 25.64 nm.

Establishment of a Cellular Model for HPV58 Pseudovirion Neutralization

HPV can hardly be cultured in vitro, and the HPV host is strongly specific. Thus, HPV can hardly be propagated in hosts other than human. That is, there was not an appropriate animal model for HPV. Therefore, in order to evaluate the immune protection of HPV vaccines quickly, it is urgent to establish an effective model for in vitro neutralization assays.

In Vitro Model of Pseudovirion Infection: by means of the characteristic that HPV VLP can package nucleic acids non-specifically, HPV pseudovirion was formed by expressing HPV L1 and L2 protein in cells, and by packaging episomal viral DNA or reporter plasmids introduced heterologously (Yeager, M. D, Aste-Amezaga, M. et al (2000) Virology (278) 570-7). The concrete methods include methods of recombinant viral expression systems and methods of co-transfection of multi-plasmids. Methods of co-transfection of multi-plasmids were used in the Example exemplarily.

In addition, some improvement directed to HPV systems were made by conventional methods as followed. The calcium phosphate transfection method for 293FT cell line was optimized to obtain a transfection efficiency of up to more than 90%, thereby facilitating large-scale production. The expression plasmid for expressing HPV structural proteins was codon-optimized to express HPV L1 and L2 gene efficiently in mammalian cells, thereby facilitating high efficient assembly of pseudovirion.

Construction of HPV Pseudovirion was as follows:

Plasmid p58L1h (the pAAV vector carrying the nucleotide sequence encoding HPV58 L1 protein (NCBI database, Accession Number: P26535.1)), plasmid p58L2h (the pAAV vector carrying the nucleotide sequence encoding HPV58 L2 protein (NCBI database, Accession Number: P26538.1)), and plasmid pN31-EGFP carrying green fluorescent protein gene, were purified by CsCl density gradient centrifugation, wherein said pN31-EGFP and said pAAV vectors were donated by Professor John T. Schiller of NIH. Methods for purifying plasmids using CsCl density gradient centrifugation were well known in the art (see The Molecular Cloning Experiment Guide, 3rd edition).

293FT cells (Invitrogen) cultured on a 10 cm cell culture plate were co-transfected with the purified p58L1h, p58L2h and pN31-EGFP (40 µg for each) by calcium phosphate transfection method. Calcium phosphate transfection method was well known in the art (see The Molecular Cloning Experiment Guide, 3rd edition). In brief, p58L1h, p58L2h and pN31-EGFP (40 µg for each) were added to the mixture of 1 mL HEPES solution (125 µL 1M HEPES pH7.3 per 50 mL deionized water, stored at 4° C.) and 1 mL 0.5M $CaCl_2$ solution. After mixing homogeneously, 2 mL 2× HeBS solution (0.28M NaCl (16.36 g), 0.05M HEPES (11.9 g), and 1.5 mM $Na_2HPO_4$ (0.213 g), dissolved in 1000 mL deionized water, pH 6.96, stored at −70° C.) was added dropwise. After standing at room temperature for 1 min, the mixture was added to the 10 cm cell culture plate where the 293FT cells were cultured. After culturing for 6 hr, the original culture medium was decanted and 10 ml fresh complete medium (Invitrogen Co.) was added. After transfection for 48 hours, the medium was decanted and the cells were washed twice with PBS. Then, the cells were collected and counted. Every $10^8$ cells were re-suspended in 1 mL lysis solution (0.25% Brij58, 9.5 mM $MgCl_2$). After lysing, cell lysate was centrifuged at 5,000 g for 10 min and the supernatant was collected. The Pseudovirion solution was obtained after adding 5M NaCl to a final concentration of 850 mM, and then was stored in small packages at −20° C.

Determination of the Neutralization Titers of Antibodies

293FT cells (Invitrogen) were plated on a 96-well cell culture plate ($1.5 \times 10^4$ cells/well). Neutralization assay was performed five hours later. Serum samples comprising antibodies to be tested were serially diluted with 10% DMEM half-by-half. The diluted samples (50 μL for each) were respectively mixed with 50 μL Pseudovirion solution diluted in 10% DMEM as prepared above (moi=0.1). After incubating at 4° C. for 1 h, the mixture was added to the 96-well cell culture plate with 293FT cells. The mixture was then incubated for 72 h at 37° C. Antibody titers of samples were estimated by observing fluorescence. Infection percentage of cells in each well was then checked by flow cytometry (EPICS XL, American Beckman Coulter Co.). The exact antibody titers of serums were calculated. Infection percentage was the percentage of cells in the positive region of the cell sample to be tested minus that in the positive region of the uninfected control cell sample.

Infection-inhibition percentage=(1−infection percentage of wells with serum/infection percentage of wells without serum)×100%

The positive region was defined as the cell region having a GFP signal determined by flow cytometry at least 10 times higher than the signal of the control cells.

Neutralization titer of antibodies was defined as the highest dilution fold under which the infection-inhibition percentage reached above 50%. Antibodies were considered as having neutralizing capacity if their infection-inhibition percentage was above 50% after 50 times dilutions.

Evaluation of Immune Protection of Vaccination of Animals with HPV58 VLPs

Rabbits were used to evaluate the immune protection of the HPV58 VLPs according to the invention. Animals for vaccination were 5 female rabbits (general grade), 6-8 weeks old, purchased from the Disease Prevention and Control Center of Guangxi province. HPV58N35C-L1 VLPs (at a concentration of 0.1 mg/ml) prepared in Example 4, were mixed with equal volume of complete Freund's Adjuvant for the first vaccination, or with equal volume of incomplete Freund's Adjuvant for the booster. The vaccination procedure was as followed: the first vaccination at Month 0, and the booster at Month 1, 2 and 3, respectively. Rabbits were vaccinated via muscle injection, with an amount of 200 μg HPV58N35C-L1 VLPs prepared in Example 4 per rabbit.

After the first vaccination, peripheral venous blood was collected every week, and serum was separated and stored for test. The neutralization titers of antibodies against HPV58 pseudovirion in the rabbit serum were determined by the method above.

The result was shown in FIG. 5. FIG. 5 showed that neutralization titers of antibodies in serum at different stages after vaccination of rabbits with HPV58N35C-L1 VLPs prepared in Example 4. It could be seen that the neutralization titers of antibodies increased significantly 2 months after the first vaccination, and reached a peak level of $10^5$ after a booster. It suggested that HPV58N35C-L1 VLPs as prepared in Example 4 had good immunogenicity, could induce the generalization of neutralization antibodies against HPV58 with a high titer in animals, and could be used as an effective vaccine for the prevention of HPV58 infection. In addition to Freund's Adjuvant, other adjuvants well known in the art might also be used in the vaccines, for example, aluminum hydroxide or aluminum phosphate adjuvants.

EXAMPLE 6

Preparation and Morphologic Observation of Other Truncated Proteins and VLPs

HPV58 L1 proteins having 5, 15, 27, 40, 60 or 70 amino acids truncated at the N-terminal, respectively, i.e. HPV58N5C-L1, HPV58N15C-L1, HPV58N27C-L1, HPV58N40C-L1, HPV58N60C-L1, HPV58N70C-L1 (their amino acid sequences were set forth in SEQ ID NOs: 2, 3, 4, 5, 6 and 7, respectively; their DNA sequences were set forth in SEQ ID NOs: 10, 11, 12, 13, 14 and 15, respectively), were prepared and purified basically by the methods as described in Examples 1-3. The proteins thus obtained had a purity of above 98% (see FIG. 6).

The purified HPV58N5C-L1, HPV58N15C-L1, HPV58N27C-L1, HPV58N40C-L1, HPV58N60C-L1, and HPV58N70C-L1 proteins were assembled into VLPs basically by the method as described in Example 4, respectively, designated as HPV58N5C-L1 VLPs, HPV58N15C-L1 VLPs, HPV58N27C-L1 VLPs, HPV58N40C-L1 VLPs, HPV58N60C-L1 VLPs, and HPV58N70C-L1 VLPs, respectively.

HPV58N5C-L1 VLPs, HPV58N15C-L1 VLPs, HPV58N27C-L1 VLPs, HPV58N40C-L1 VLPs, HPV58N60C-L1 VLPs, and HPV58N70C-L1 VLPs were subjected to transmission electron microscopy and dynamic light scattering observation basically by the method as described in Example 5, respectively. The results were shown in FIG. 7 and FIG. 8. FIG. 7 showed that the truncated proteins could form a large number of VLPs with a radius of about 25 nm, wherein the particle size was consistent with the theoretic size and the particles were homogenous. FIG. 8 showed that HPV58N5C-L1, HPV58N15C-L1, HPV58N27C-L1, HPV58N40C-L1, HPV58N60C-L1, and HPV58N70C-L1 VLPs had a hydrodynamic radius of about 25 nm and a particle assembly rate of 100%.

In addition, it was demonstrated by the method as described in Example 5 that the HPV58N5C-L1, HPV58N15C-L1, HPV58N27C-L1, HPV58N40C-L1, HPV58N60C-L1, and HPV58N70C-L1 VLPs obtained in the invention also had good immunogenicity, could induce the generalization of neutralization antibodies with a high titer in animals, and therefore could be used as an effective vaccine for the prevention of HPV infection.

Although the specific embodiments of the present invention have been described in details, those skilled in the art would understand that, according to the teachings disclosed in the specification, various modifications and changes can be made without departing from the sprit or scope of the present invention as generally described, and that such modifications and changes are within the scope of the present invention. The scope of the present invention is given by the appended claims and any equivalents thereof.

The invention claimed is:

1. An *Escherichia coli* (*E. coli*) expression vector encoding a truncated human papillomavirus 58 (HPV58) L1 protein, wherein said truncated HPV58 L1 protein is different from wild type HPV58 L1 protein in that the first 35, 40, 60, or 70 amino acids at the N-terminal of the wild type HPV58 L1 protein are substituted with a methionine residue encoded by an initiator codon.

2. An *E. coli* host cell comprising the expression vector according to claim 1.

3. A method for obtaining a truncated HPV58 L1 protein, comprising:
 a) expressing a truncated HPV58 L1 protein in an *E. coli* expression system, wherein said truncated HPV58 L1 protein is different from wild type HPV58 L1 protein in that the first 35, 40, 60 or 70 amino acids at the N-terminal of the wild type HPV58 L1 protein are substituted with a methionine residue encoded by an initiator codon; and
 b) carrying out a purification process on a lysis supernatant containing said truncated HPV58 L1 protein.

4. A method for preparing a HPV58 virus-like particle comprising a truncated HPV58 L1 protein, wherein said truncated HPV58 L1 protein is different from the wild type HPV58 L1 protein in that the first 35, 40, 60 or 70 amino acids at the N-terminal of the wild type HPV58 L1 protein are substituted with a methionine residue encoded by an initiator codon, comprising the steps of:
 a) expressing the truncated HPV58 L1 protein in *E. coli*;
 b) disrupting the E. coli, which has expressed the truncated HPV58 L1 protein in a solution at a salt concentration of 100 mM to 600mM, and isolating the supernatant;
 c) decreasing the salt concentration of the supernatant of b) to 100mM or less by using water or a solution at a low salt concentration and collecting a precipitate;
 d) re-dissolving the precipitate of c) in a solution at a salt concentration of 150mM to 2500mM and adding a reductant to the solution, and then isolating the resultant solution, wherein the resultant solution contains the truncated HPV58 L1 protein with a purity of at least 50%;
 e) purifying the truncated HPV58 L1 protein with a purity of at least 50% as obtained in d) by a chromatography; and
 f) removing reductant from the protein obtained in e).

5. The method of claim 3, wherein said truncated HPV58 L1 protein consists of an amino acid sequence selected from the group consisting of amino acid sequences as set forth in SEQ ID NO: 1, SEQ ID NO: 5, SEQ ID NO: 6, and SEQ ID NO: 7.

6. A method for obtaining a truncated HPV58 L1 protein, comprising steps of:
  a) expressing a truncated HPV58 L1 protein in E. coli, wherein said truncated HPV58 L1 protein has 35, 40, 60, or 70 amino acids truncated at its N-terminal, as compared with wild type HPV58 L 1 protein, and wherein said truncated HPV58 L 1 protein results from substituting the first 35, 40, 60, or 70 amino acids at the N-terminal of the wild type HPV58 L 1 protein with a methionine residue encoded by an initiator codon;
  b) disrupting the E. coli, which has expressed the truncated HPV58 L 1 protein, in a solution at a salt concentration of 100mM to 600mM, and isolating the supernatant;
  c) decreasing the salt concentration of the supernatant of b) to 100 mM or less, by using water or a solution at a low salt concentration, and collecting a precipitate;
  d) re-dissolving the precipitate of c) in a solution at a salt concentration of 150mM to 2500 mM and adding a reductant to the solution, and then isolating the resultant solution, wherein the solution contains the truncated HPV58 L 1 protein with a purity of at least 50%.

7. The E. coli expression vector of claim 1, wherein said truncated HPV58 L 1 protein consists of an amino acid sequence selected from the group consisting of amino acid sequences as set forth in SEQ ID NO: 1, SEQ ID NO: 5, SEQ ID NO: 6, and SEQ ID NO: 7.

8. The method of claim 4, wherein said truncated HPV58 L 1 protein consists of an amino acid sequence selected from the group consisting of amino acid sequences as set forth in SEQ ID NO: 1, SEQ ID NO: 5, SEQ ID NO: 6, and SEQ ID NO: 7.

9. The method of claim 6, wherein said truncated HPV58 L 1 protein consists of an amino acid sequence selected from the group consisting of amino acid sequences as set forth in SEQ ID NO: 1, SEQ ID NO: 5, SEQ ID NO: 6, and SEQ ID NO: 7.

* * * * *